United States Patent
Wortmann et al.

(10) Patent No.: US 7,426,567 B2
(45) Date of Patent: Sep. 16, 2008

(54) METHODS AND APPARATUS FOR STREAMING DICOM IMAGES THROUGH DATA ELEMENT SOURCES AND SINKS

(75) Inventors: Joseph P. Wortmann, Birmingham, AL (US); Gary York, Birmingham, AL (US)

(73) Assignee: Emageon Inc., Birmingham, AL (US)

( * ) Notice: Subject to any disclaimer, the term of this patent is extended or adjusted under 35 U.S.C. 154(b) by 633 days.

(21) Appl. No.: 09/947,055

(22) Filed: Sep. 4, 2001

(65) Prior Publication Data
US 2003/0149680 A9    Aug. 7, 2003

Related U.S. Application Data

(60) Provisional application No. 60/229,562, filed on Sep. 2, 2000.

(51) Int. Cl.
*G06F 15/16* (2006.01)
(52) U.S. Cl. .................. 709/231; 709/223; 709/232
(58) Field of Classification Search .......... 709/200, 709/206, 231, 232, 223
See application file for complete search history.

(56) References Cited

U.S. PATENT DOCUMENTS

| | | | |
|---|---|---|---|
| 4,720,678 | A | 1/1988 | Glover et al. |
| 4,817,050 | A | 3/1989 | Komatsu et al. |
| 4,833,625 | A | 5/1989 | Fisher et al. |
| 4,835,532 | A | 5/1989 | Fant |
| 4,958,283 | A | 9/1990 | Tawara et al. |
| 5,016,193 | A | 5/1991 | Stone et al. |
| 5,025,396 | A | 6/1991 | Parks et al. |
| 5,117,351 | A | 5/1992 | Miller |
| 5,119,444 | A | 6/1992 | Nishihara |
| 5,150,427 | A | 9/1992 | Frazee et al. |
| 5,233,299 | A | 8/1993 | Souza et al. |
| 5,235,418 | A | 8/1993 | Lucas |

(Continued)

FOREIGN PATENT DOCUMENTS

EP    0 833 266 A2    4/1998

(Continued)

OTHER PUBLICATIONS

National Electrical Manufacturers Association, "Digital Imaging and Communications in Medicine (DICOM)", Year 1999-2000, Part 1, 7, and 11.*

(Continued)

*Primary Examiner*—John Follansbee
*Assistant Examiner*—Nghi V Tran
(74) *Attorney, Agent, or Firm*—Kilpatrick Stockton LLP

(57) ABSTRACT

Methods and apparatus for streaming DICOM images or objects through data element sources and sinks. Digital data contained in relatively large DICOM objects of any size can be transmitted between applications, devices, or storage media in a network. The use of data element sources and data element sinks to incrementally process data elements and data values one at a time, minimizes the amount of memory needed to perform a DICOM operation. The methods and apparatus according to the present invention limit the consumption of memory resources while providing a relatively small, fixed amount of memory for handling a relatively large DICOM object, while maintaining the performance of applications operating in the DICOM network.

39 Claims, 11 Drawing Sheets

U.S. PATENT DOCUMENTS

| | | |
|---|---|---|
| 5,241,472 A | 8/1993 | Gur et al. |
| 5,261,012 A | 11/1993 | Hardy et al. |
| 5,276,805 A | 1/1994 | Hamaguchi |
| 5,289,577 A | 2/1994 | Gonzales et al. |
| 5,301,271 A | 4/1994 | Hiratsuka et al. |
| 5,313,567 A | 5/1994 | Civanlar et al. |
| 5,319,777 A | 6/1994 | Perez |
| 5,321,520 A | 6/1994 | Inga et al. |
| 5,321,776 A | 6/1994 | Shapiro |
| 5,331,552 A | 7/1994 | Lloyd et al. |
| 5,339,433 A | 8/1994 | Frid-Nielsen |
| 5,347,384 A | 9/1994 | McReynolds et al. |
| 5,359,512 A | 10/1994 | Nishihara |
| 5,359,724 A | 10/1994 | Earle |
| 5,384,900 A | 1/1995 | Sato et al. |
| 5,408,659 A | 4/1995 | Cavendish et al. |
| 5,415,167 A | 5/1995 | Wilk |
| 5,440,685 A | 8/1995 | Takiyama et al. |
| 5,452,287 A | 9/1995 | DiCecco et al. |
| 5,465,306 A | 11/1995 | Van Lier |
| 5,469,353 A | 11/1995 | Pinsky et al. |
| 5,481,601 A | 1/1996 | Nazif et al. |
| 5,485,507 A | 1/1996 | Brown et al. |
| 5,499,297 A | 3/1996 | Boebert |
| 5,513,101 A | 4/1996 | Pinsky et al. |
| 5,537,630 A | 7/1996 | Berry et al. |
| 5,542,003 A | 7/1996 | Wofford |
| 5,544,302 A | 8/1996 | Nguyen |
| 5,548,727 A | 8/1996 | Meehan |
| 5,557,542 A | 9/1996 | Asahina et al. |
| 5,581,460 A | 12/1996 | Kotake et al. |
| 5,583,656 A | 12/1996 | Gandhi et al. |
| 5,586,262 A | 12/1996 | Komatsu et al. |
| 5,592,666 A | 1/1997 | Perez |
| 5,603,323 A | 2/1997 | Pflugrath et al. |
| 5,619,571 A | 4/1997 | Sandstrom et al. |
| 5,655,084 A | 8/1997 | Pinsky et al. |
| 5,668,998 A | 9/1997 | Mason et al. |
| 5,671,353 A | 9/1997 | Tian et al. |
| 5,699,360 A | 12/1997 | Nishida et al. |
| 5,737,549 A | 4/1998 | Hersch et al. |
| 5,740,267 A | 4/1998 | Echerer et al. |
| 5,740,428 A | 4/1998 | Mortimore et al. |
| 5,751,783 A | 5/1998 | Granfors et al. |
| 5,752,243 A | 5/1998 | Reiter et al. |
| 5,778,177 A | 7/1998 | Azar |
| 5,835,735 A * | 11/1998 | Mason et al. ............... 710/107 |
| 5,838,906 A | 11/1998 | Doyle et al. |
| 5,838,970 A | 11/1998 | Thomas |
| 5,845,018 A | 12/1998 | Breish |
| 5,848,416 A | 12/1998 | Tikkanen |
| 5,851,186 A | 12/1998 | Wood et al. |
| 5,883,985 A | 3/1999 | Pourjavid |
| 5,884,016 A | 3/1999 | Allen et al. |
| 5,918,232 A | 6/1999 | Pouschine et al. |
| 5,923,789 A | 7/1999 | Avinash |
| 5,944,659 A | 8/1999 | Flach et al. |
| 5,950,207 A | 9/1999 | Mortimore et al. |
| 5,966,463 A | 10/1999 | Wang |
| 5,971,923 A | 10/1999 | Finger |
| 5,986,662 A | 11/1999 | Argiro et al. |
| 6,003,036 A | 12/1999 | Martin |
| 6,014,671 A | 1/2000 | Castelli et al. |
| 6,042,545 A | 3/2000 | Hossack et al. |
| 6,047,081 A | 4/2000 | Groezinger et al. |
| 6,047,324 A | 4/2000 | Ford et al. |
| 6,047,381 A | 4/2000 | Klein |
| 6,055,000 A | 4/2000 | Okada |
| 6,057,937 A | 5/2000 | Shimizu et al. |
| 6,072,914 A | 6/2000 | Mikuni |
| 6,083,162 A | 7/2000 | Vining |
| 6,101,407 A | 8/2000 | Groezinger |
| 6,108,697 A | 8/2000 | Raymond et al. |
| 6,115,150 A | 9/2000 | Nakamura et al. |
| 6,115,486 A | 9/2000 | Cantoni |
| 6,117,079 A | 9/2000 | Brackett et al. |
| 6,122,636 A | 9/2000 | Malloy et al. |
| 6,137,527 A | 10/2000 | Abdel-Malek et al. |
| 6,137,856 A | 10/2000 | Lin |
| 6,141,398 A | 10/2000 | He et al. |
| 6,157,337 A | 12/2000 | Sato |
| 6,157,929 A | 12/2000 | Zamiska et al. |
| 6,171,244 B1 | 1/2001 | Finger et al. |
| 6,178,225 B1 | 1/2001 | Zur et al. |
| 6,195,093 B1 | 2/2001 | Nelson et al. |
| 6,198,283 B1 | 3/2001 | Foo et al. |
| 6,204,853 B1 | 3/2001 | Cline et al. |
| 6,210,327 B1 | 4/2001 | Brackett et al. |
| 6,213,945 B1 | 4/2001 | Tynan |
| 6,215,903 B1 | 4/2001 | Cook |
| 6,219,061 B1 | 4/2001 | Lauer et al. |
| 6,222,841 B1 | 4/2001 | Taniguchi |
| 6,224,551 B1 | 5/2001 | Mullen |
| 6,233,279 B1 | 5/2001 | Boon |
| 6,243,441 B1 | 6/2001 | Zur |
| 6,260,021 B1 | 7/2001 | Wong et al. |
| 6,262,749 B1 | 7/2001 | Finger et al. |
| 6,266,081 B1 | 7/2001 | Ono et al. |
| 6,266,733 B1 | 7/2001 | Knittell et al. |
| 6,272,469 B1 | 8/2001 | Koritzinsky et al. |
| 6,272,470 B1 | 8/2001 | Teshima |
| 6,287,258 B1 * | 9/2001 | Phillips ..................... 600/437 |
| 6,297,799 B1 | 10/2001 | Knittel et al. |
| 6,314,366 B1 | 11/2001 | Farmakis et al. |
| 6,314,452 B1 | 11/2001 | Dekel et al. |
| 6,584,461 B1 * | 6/2003 | Patel et al. ..................... 707/3 |
| 6,603,494 B1 * | 8/2003 | Banks et al. ................ 715/807 |
| 6,731,798 B1 * | 5/2004 | Stearns ..................... 382/172 |
| 6,775,346 B2 | 8/2004 | Heuscher et al. |
| 6,912,317 B1 * | 6/2005 | Barnes et al. ............... 382/239 |
| 6,937,767 B1 * | 8/2005 | Burak et al. ................ 382/232 |
| 7,028,182 B1 * | 4/2006 | Killcommons ............. 713/161 |
| 2001/0001020 A1 | 5/2001 | Mizuno |
| 2002/0004798 A1 * | 1/2002 | Babula et al. ............ 707/104.1 |
| 2002/0021829 A1 * | 2/2002 | Doi et al. ................... 382/131 |
| 2003/0059096 A1 * | 3/2003 | Dekel et al. ................ 382/131 |
| 2003/0105393 A1 * | 6/2003 | Sutherland et al. ......... 600/407 |
| 2003/0229282 A1 * | 12/2003 | Burdette et al. ............ 600/439 |
| 2004/0081435 A1 * | 4/2004 | Maehashi et al. .......... 386/111 |
| 2005/0271283 A1 * | 12/2005 | Dekel et al. ................ 382/232 |

FOREIGN PATENT DOCUMENTS

| | | |
|---|---|---|
| EP | 0 876 033 A | 11/1998 |
| EP | 0 964 559 A | 12/1999 |
| JP | 4-30263 | 2/1992 |
| JP | 5-81354 | 4/1993 |
| JP | 5-89006 | 4/1993 |
| JP | 5-242158 | 9/1993 |
| JP | 7-44341 | 2/1995 |
| JP | 8-173417 | 7/1996 |
| JP | 8-315119 | 11/1996 |
| JP | 9-248280 | 9/1997 |
| JP | 10099282 | 4/1998 |
| JP | 10-154987 | 6/1998 |
| JP | 11-27680 | 1/1999 |
| JP | 11-239165 | 8/1999 |
| JP | 11-250160 | 9/1999 |
| JP | 11-284974 | 10/1999 |
| JP | 11-341483 | 12/1999 |
| JP | 2000-29971 | 1/2000 |
| JP | 2000-116606 | 4/2000 |
| JP | 2000-287013 | 10/2000 |

| JP | 2000-306018 | 11/2000 |

OTHER PUBLICATIONS

Lindblad, Christopher, J., et al., "The VuSystem: A Programming System for Visual Processing of Digital Video," *Multimedia 94*, pp. 307-314, Oct. 1994.

Campbell, Andrew, et al., "A Continuous Media Transport and Orchestration Service," *COMM'92*, pp. 99-110, Aug. 1992.

Press Release, "RealTimeImage's iPACS integrated into Wuestec's Digital Radiography suite for real time Internet Image Delivery," Virtual Medical Worlds, http://www.hoise.com/vmw/01/articles/vmw/LV-VM-05-01-9.html.

"Digital Imaging and Communications in Medicine (DICOM): Part 1: Intro. and Overview," *NEMA Standards Publication PS31.1(199x)*, pp. 1-7, 9, 11, 13, 15, Mar. 27, 1992.

"Out of Digital Storage Already?", WamlNet Medical brochure.

Press Release, "RealTimeImage and Kodak's Health Imaging Division Announce Licensing Agreement," http://www.realtimeimage.com/MedicalImageing/mednews_nov7_00.asp.

"Data Sources and 'data sinks'," http://www.herdsoft.com/ti/davincie/imex8qip.htm.

Erikson, B.J., "Irreversible Compression of Medical Images", released by the Society for Computer Applications in Radiology at the 83$^{rd}$ meeting of the Radiological Society of North America, pp. 1-9, Nov. 26-Dec. 1, 2000.

Levoy, M., "Display of Surfaces from Volume Data", IEEE Computer Graphics and Applications, pp. 29-37, May 1988.

Wallace, G.K., "The JPEG Still Picture Compression Standard", IEEE-Transactions on Consumer Electronics, pp. 1-16, Dec. 1991.

Liu, J, et al., "Flexible Storage Placement of Digital Video Media," Proceedings of INFOCOM '95—Conference on Computer Communications, vol. 2, Conf. 14, Apr. 2, 1995, pp. 788-795, XP000580649.

Negishi, Y et al., "A portable communication system for video-on-demand applications using the existing infrastructure," Proceedings of IEEE INFOCOM, L, vols. 2, Conf. 15, Mar. 24, 1996, pp. 18-26.

Nema: "DICOM Part 8: Network Communication Support for Message Exchange," Aug. 20, 1999, pp. 1-57, XP002203931.

Nema: "DICOM Part 5: Data Structures and Encoding," Aug. 20, 1999, pp. 1-80, XP002203932.

Von Land, C., et al. "Object-oriented Design of the DICOM Standard and its Application to Cardiovascular Imaging," IEEE, Computer in Cardiology, vols. 24, 1997, pp. 645-648.

International Search Report for PCT/US01/27465, mailed Jul. 16, 2002.

DICOM & HIS/RIS Connectivity, "ExamWorks" and "MergeMVP" www.merge.com/products/dicomhisriseconnectivity/index.asp.

DICOM & HIS/RIS Connectivity, "ExamWorks+," www.merge.com/products/dicomhisriseconnectivity/extendedconversion.asp.

Dicom.offis.de—DICOM Software made by OFFIS—DICOMscope—DICOM Viewer, "DICOMscope—DICOM," http://dicom.offis.de/dscope, (2pages).

MIR DICOM Central Test Node Software, "Electronic Radiology Laboratory Mallinckrodt Institute of Radiology," http://wuerlim.wustl.edu/DICOM/ctn.html.

Softlink Java DICOM Toolkit, "Java Dicom Toolkit Features," http://www.softlink.be/jdt/features.htm.

Technology>Conformance Statement, :Technology, http://www.mitra.com/technology/conformance.html.

Medical Image Format FAQ—Part 8, "DICOM Information Sources," http://www.dclunie.com/medical-image-faq/html/part8.html (31 pages).

"DICOM PS3.4", 1999.

"DICOM PS3.5", 1999.

"DICOM PS3.7", 1998.

"DICOM PS3.8", 1998.

"Information Technology—Open Systems Interconnection—Basic Reference Model: The Basic Model", *International Standard ISO/IEC 7498-1* Second Edition Nov. 15, 1994.

"J2SE c 1.2.2 Documentation", 1999.

"Product Overview of the DICOM Standards", *National Electrical Manufacturers Association* Rosslyn, Virginia 1998, 1-6.

"PS 3.3 DICOM Part 3: Information Object Definitions", *National Electrical Manufacturers Association* Rosslyn, Virginia 1999, 1-568.

Horstmann, Cay S. et al., "Core Java 1.2, vol. I—Fundamentals", 1999.

Morgan, Mike et al., "Using Java 1.2", Jun. 1998.

\* cited by examiner

First 128 bytes: unused by DICOM format
Followed by the characters 'D','I','C','M'
This preamble is followed by extra information e.g.:

0002,0000,File Meta Elements Group Len: 132
0002,0001,File Meta Info Version: 256
0002,0010,Transfer Syntax UID: 1.2.840.10008.1.2.1.
0008,0000,Identifying Group Length: 152
0008,0060,Modality: MR
0008,0070,Manufacturer: MRIcro
0018,0000,Acquisition Group Length: 28
0018,0050,Slice Thickness: 2.00
0018,1020,Software Version: 46\64\37
0028,0000,Image Presentation Group Length: 148
0028,0002,Samples Per Pixel: 1
0028,0004,Photometric Interpretation: MONOCHROME2.
0028,0008,Number of Frames: 2
0028,0010,Rows: 109
0028,0011,Columns: 91
0028,0030,Pixel Spacing: 2.00\2.00
0028,0100,Bits Allocated: 8
0028,0101,Bits Stored: 8
0028,0102,High Bit: 7
0028,0103,Pixel Representation: 0
0028,1052,Rescale Intercept: 0.00
0028,1053,Rescale Slope: 0.00392157
7FE0,0000,Pixel Data Group Length: 19850
7FE0,0010,Pixel Data: 19838

Figure 8

METHODS AND APPARATUS FOR STREAMING DICOM IMAGES THROUGH DATA ELEMENT SOURCES AND SINKS

CROSS-REFERENCE TO RELATED APPLICATION

This application claims the benefit of U.S. Provisional Patent Application No. 60/229,562, filed Sep. 2, 2000, now abandoned.

FIELD OF THE INVENTION

The present invention relates in general to image transmission, and relates more particularly to methods and apparatus for streaming DICOM images through data element sources and sinks.

BACKGROUND OF THE INVENTION

Medical images can be communicated between computers using a network protocol standard named Digital Imaging and Communications in Medicine (DICOM). The DICOM network protocol was created to aid the distribution and viewing of medical images and objects such as EKG waveforms, computed tomography (CT), magnetic resonance (MR), and ultrasound.

The DICOM network protocol defines a format used to store, receive, and transmit digital image data and objects. The DICOM object format typically contains a header and image data. The header contains information about the patient's name, type of medical procedure or scan, image dimensions, etc. For example, a DICOM image file includes a header which contains data that describe the physical dimensions of a medical image. The header can also include data that contains textual information about a scan contained in the image. The size of a header may vary depending upon the amount of information that is stored in the image. The data in a header can be organized as one or more groups. One group may be a meta file information group which defines one or more data elements such as a group length, a file version, and a transfer syntax. The number of data elements depends upon the image type and the characteristics of the particular image type.

Object data typically follows the header data. The object data can have data elements which define characteristics of the particular object type and the object data associated with the particular object type. The object data can include information obtained in a medical scan performed in two and/or three dimensions. For example, a magnetic resonance image (MRI) may have DICOM image data that includes a data element that specifically defines the MRI echo time. Furthermore, image data may be compressed or encapsulated to reduce the image file size.

Most DICOM data elements are small and bounded in size by the type of data that they can contain. For example, integer data elements may only contain a few integers. These data elements are always relatively small and do not have a significant or large impact on the performance and scalability of a network because of their relatively small size. Other types of DICOM data elements such as image data can be relatively large in comparison. Two types of DICOM data elements warrant special attention since they can be large: sequences and pixel data. Sequences in DICOM are a type of data element that can recursively contain other data sets. Since they can contain other data sets, they could potentially be relatively large if they contain a very large number of small data elements, or if they contain pixel data. Pixel data is a type of data element that corresponds to actual image data. Pixel data is a type of data element that can be relatively large, and in some cases, extremely large. In cases where a very large data set is being communicated, almost all of the bytes in the data set may be pixel data. Most other types of data elements communicate information about the image (metadata) such as the patient name, type of image, and image date and time.

DICOM communicates by transmitting data sets. A data set is an ordered set of data elements, such as sequence data, pixel data, or other types of data. Each data element represents information that is being communicated. Each data element has a particular type, and can vary in size depending upon the data element type. For example, by way of illustration of the different range in the size of an image file, the file size of a DICOM image can range from approximately 128 kilobytes (KB) for a single DICOM image, or up to approximately 600 megabytes (MB) for a time-sequence or multi-frame DICOM image.

DICOM data sets are communicated using one or more transfer syntaxes. A transfer syntax specifies a type of encoding of the data for the particular data set. The DICOM network protocol can support at least three types of transfer syntax: little endian explicit value representation, little endian implicit value representation, and big endian explicit value representation.

A unique feature of DICOM network protocol allows data to be transformed into a different form when transported. This unique feature of DICOM data transformation during the transmission of DICOM images over a conventional DICOM network creates a relatively large demand for the memory resources in a DICOM network.

The DICOM network protocol consists of multiple layers. The DICOM network protocol can also be built on top of a standard TCP/IP protocol. When transmitting data over a communications network, the DICOM protocol breaks a data set into one or more data packets before sending it across the network. Each data packet defines one or more protocol data units (PDUs). If an underlying protocol layer transforms the data into data packets, as in TCP/IP protocol, the DICOM protocol requires that the data sets being communicated across the network also be packaged as protocol data units (PDUs). For example, when the DICOM network protocol runs on top of the TCP/IP protocol, this effectively double packetizes the data. That is, DICOM packages the data sets as protocol data units (PDUs) and TCP/IP packages the data sets as data packets. This type of DICOM/TCP/IP layered protocol structure creates a relatively large demand for memory resources in a conventional DICOM network. Moreover, the transmission of DICOM images through multiple layers of the DICOM network protocol can also create a relatively large demand for memory resources in a conventional DICOM network.

The DICOM protocol follows a strict order for establishing and maintaining communications. A state machine operated by the Upper Service Level layer of the DICOM protocol specifies a strict order for establishing and maintaining communications between two devices in a DICOM network. For example, since the DICOM protocol is connection oriented, no communication of DICOM data can occur until a DICOM association or connection has been established between two devices. That is, at least two DICOM protocol-based devices must be in communication with each other in order to establish a DICOM association or connection. After a DICOM association or connection has been established, communication must continue to follow a strict order, and then the DICOM association or connection must be closed in an orderly fashion. Such a strict order dictated by the DICOM network protocol can create a relatively large demand for memory resources in a conventional DICOM network.

Each DICOM association or connection can be used to perform DICOM data operations in the DICOM network. DICOM operations can be performed sequentially, or one after another, or concurrently. Concurrent operations are called asynchronous operations per association in DICOM. Conventional DICOM networks typically handle multiple concurrent or asynchronous operations involving DICOM data, and large DICOM file sizes can create a relatively large demand for memory resources in a conventional DICOM network.

The rapid handling of relatively large objects by conventional DICOM communication networks demands that DICOM protocol operations be performed in an efficient, high performance manner. Conventional DICOM communication networks suffer a significant drop in the speed and performance when handling relatively large DICOM object files. Since DICOM objects tend to be relatively large, communication of DICOM objects can quickly overwhelm a communications network that is not designed to accommodate such large image objects. Conventional DICOM communication networks rely upon servers to handle multiple and simultaneous DICOM operations. In cases where a single DICOM file or storage operation could consume a large portion of a server's resources such as a memory and processing time, a DICOM server may suffer from poor scalability and performance when handling such large objects. The network and server performance problems can worsen significantly when multiple clients attempt to simultaneously or concurrently use the network.

Therefore, there is a need for methods and apparatus for limiting the consumption of memory resources during the handling of DICOM objects in a network.

There is a further need for methods and apparatus for allowing one or more applications in a DICOM communications network to limit memory usage regardless of the size of DICOM objects to be communicated in the network.

There is a further need for improved methods and apparatus for transmitting digital data between two devices in a communications network.

There is a further need for improved methods and apparatus for transmitting DICOM objects in a network while maintaining or improving the performance of one or more applications operating in the network.

There is a further need for methods and apparatus for streaming DICOM objects in a network through a data element source and data element sink.

SUMMARY OF THE INVENTION

The invention addresses the problems above by providing methods and apparatus for streaming DICOM objects in a network through data element sources and data element sinks. Methods and apparatus according to the present invention limit the consumption of memory resources during the handling of DICOM objects in a network. Furthermore, methods and apparatus according to the present invention permit one or more applications in a DICOM communications network to limit memory usage regardless of the size of DICOM objects to be communicated in the network. Moreover, methods and apparatus according to the present invention permit transmission digital data between two devices in a communications network. Finally, methods and apparatus according to the present invention permit transmission of DICOM objects in a network while maintaining or improving the performance of one or more applications operating in the network.

Methods and apparatus according to the present invention permit the transmission of digital data between two devices in a communications network using a fixed amount of memory. For example, methods and apparatus according to the present invention permit streaming DICOM objects of relatively large file size between two devices in a DICOM network using only a limited, fixed size of memory. To handle a DICOM object or any other digital data or object of relatively large file size, methods and apparatus according to the present invention apportion the object into small, fixed portions of data elements. The methods and apparatus according to the present invention then limit the number of data elements that can be stored in memory at a single time for a single operation. Each data element is then handled incrementally by a data element source or data element sink to avoid using too much memory for a single operation. Thus, the methods and apparatus according to the present invention permit a DICOM communications network to stream a DICOM object or image using only a small, fixed amount of memory regardless of the size of the DICOM object or image that is being communicated.

In a first exemplary method for communicating digital data from a first device to a second device using a fixed amount of memory, the method initially defines a limited number of data values to be stored in a data stream. Next, the method incrementally reads a set of data elements from a first device so that each data element is read one at a time. Subsequently, a data value is extracted from each data element. If a data element is larger than a threshold size, then the data can be transmitted in relatively small, fixed size portions of data. Finally, the method transmits the data stream containing a predefined limited number of data values to a second device so that data values can be encoded to the second device.

In another exemplary method for communicating digital data from a first device to a second device using a fixed amount of memory, the present invention may receive a file containing digital data from a first device. Next, the method creates a data stream containing data values for the file containing digital data. Based on the data stream, the present invention creates a data element source. The method can then incrementally process the data elements one at a time from the data stream through the data element source. Finally, the data elements are transmitted to a data element sink which encodes the data elements to a second device.

An exemplary embodiment of an apparatus of the present invention includes a communications module for streaming digital data between two devices in a network using a fixed amount of memory. The communications module includes a data element source and a communications engine. The data element source is configured for receiving a set of data elements from a first device. The data element source is also configured for incrementally processing a single data element at a time from the set of data elements. The communications engine is configured for extracting data values from the data elements and creating a data stream from the extracted data values by passing them to the data element sink which encodes them to the second device. Moreover, the communications engine is further configured for transmitting the data stream containing the extracted data values to a second device.

Another exemplary embodiment of an apparatus of the present invention includes a communications module for streaming digital data between two devices in a network using a fixed amount of memory. The communications module includes a data element sink and a communications engine. The data element sink is configured for receiving a set of data elements from a first device. The data element sink is also configured for incrementally writing a single data element at a time from the set of data elements. The communications engine is configured for extracting data values from the data elements and creating a data stream from the extracted data values. Moreover, the communications engine is further configured for transmitting the data stream containing the extracted data values to a second device.

Thus, as described in the methods and apparatus of the present invention, digital data contained in relatively large DICOM objects of any size can be transmitted between applications, devices, or storage media in a network. The use of data element sources and data element sinks to incrementally process data elements and data values one at a time, minimizes the amount of memory needed to perform a DICOM operation. The methods and apparatus according to the present invention limit the consumption of memory resources while providing a relatively small, fixed amount of memory for handling a relatively large DICOM object, while maintaining the performance of applications operating in the DICOM network.

BRIEF DESCRIPTION OF THE DRAWINGS

FIG. 8 illustrates data contained in a DICOM image file.

DETAILED DESCRIPTION OF EMBODIMENTS OF THE INVENTION

Figure 1:
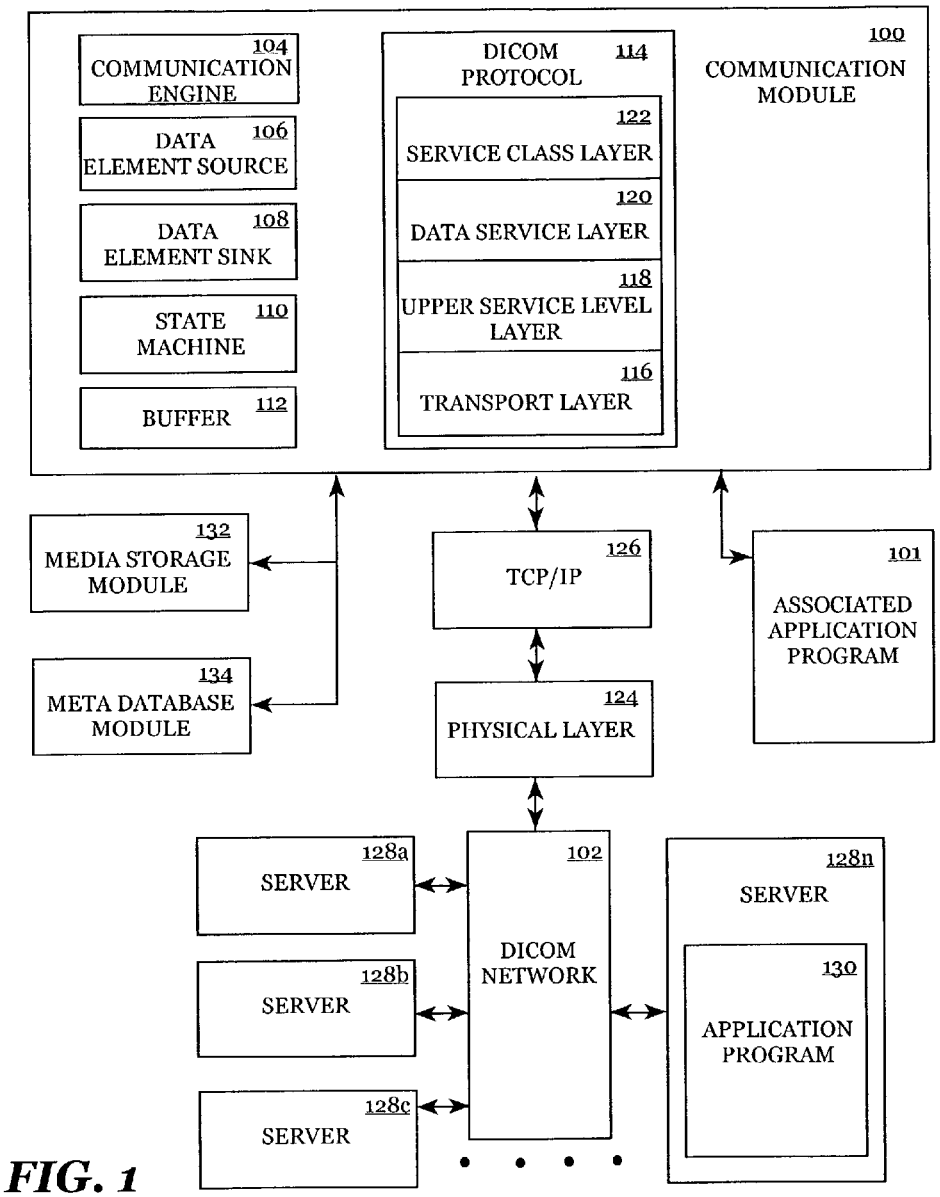
FIG. 1 is a functional block diagram of a system according to an exemplary embodiment of the present invention.

Particular embodiments of the present invention will now be described in greater detail with reference to the drawings.

In a first exemplary method for communicating digital data from a first device to a second device using a fixed amount of memory, the method initially defines a limited number of data values to be stored in a data stream. Next, the method incrementally reads a set of data elements from a first device so that each data element is read one at a time. Subsequently, a data value is extracted from each data element. If a data element is larger than a threshold size, then the data can be transmitted in relatively small, fixed size portions of data. Finally, the method transmits the data stream containing a predefined limited number of data values to a second device so that data values can be encoded to the second device.

In another exemplary method for communicating digital data from a first device to a second device using a fixed amount of memory, the present invention may receive a file containing digital data from a first device. Next, the method creates a data stream containing data values for the file containing digital data. Based on the data stream, the present invention creates a data element source. The method can then incrementally process the data elements one at a time from the data stream through the data element source. Finally, the data elements are transmitted to a data element sink which encodes the data elements to a second device.

An exemplary embodiment of an apparatus of the present invention includes a communications module for streaming digital data between two devices in a network using a fixed amount of memory. The communications module includes a data element source and a communications engine. The data element source is configured for receiving a set of data elements from a first device. The data element source is also configured for incrementally processing a single data element at a time from the set of data elements. The communications engine is configured for extracting data values from the data elements and creating a data stream from the extracted data values by passing them to the data element sink which encodes them to the second device. Moreover, the communications engine is further configured for transmitting the data stream containing the extracted data values to a second device.

Another exemplary embodiment of an apparatus of the present invention includes a communications module for streaming digital data between two devices in a network using a fixed amount of memory. The communications module includes a data element sink and a communications engine. The data element sink is configured for receiving a set of data elements from a first device. The data element sink is also configured for incrementally writing a single data element at a time from the set of data elements. The communications engine is configured for extracting data values from the data elements and creating a data stream from the extracted data values. Moreover, the communications engine is further configured for transmitting the data stream containing the extracted data values to a second device.

FIG. 1 illustrates a functional block diagram of a system according to an exemplary embodiment of present invention. The system comprises a communications module 100. The communications module 100 is configured for the transmission or streaming of objects between an associated application program 101 and another application program via a network. Furthermore, the communications module 100 is configured for the transmission or streaming of DICOM objects including DICOM image files or other similar types of digital images between an associated application program 101 and another application program via a network. For example, the communications module 100 can communicate between an associated application program 101 and an application program 130 via a communications network such as a DICOM network 102 to send or receive DICOM objects including DICOM image files or other similar types of digital objects.

Note that the communications module 100 generally communicates between a Service Class Provider (SCP) and a Service Class User (SCU). A SCP receives a request for a DICOM network protocol-defined service, while a SCU initiates a request for a DICOM network protocol-defined service. For example, an associated application program 101 can be a SCU, and a server 128a-n executing an application program 130 can be a SCP.

Figure 7:
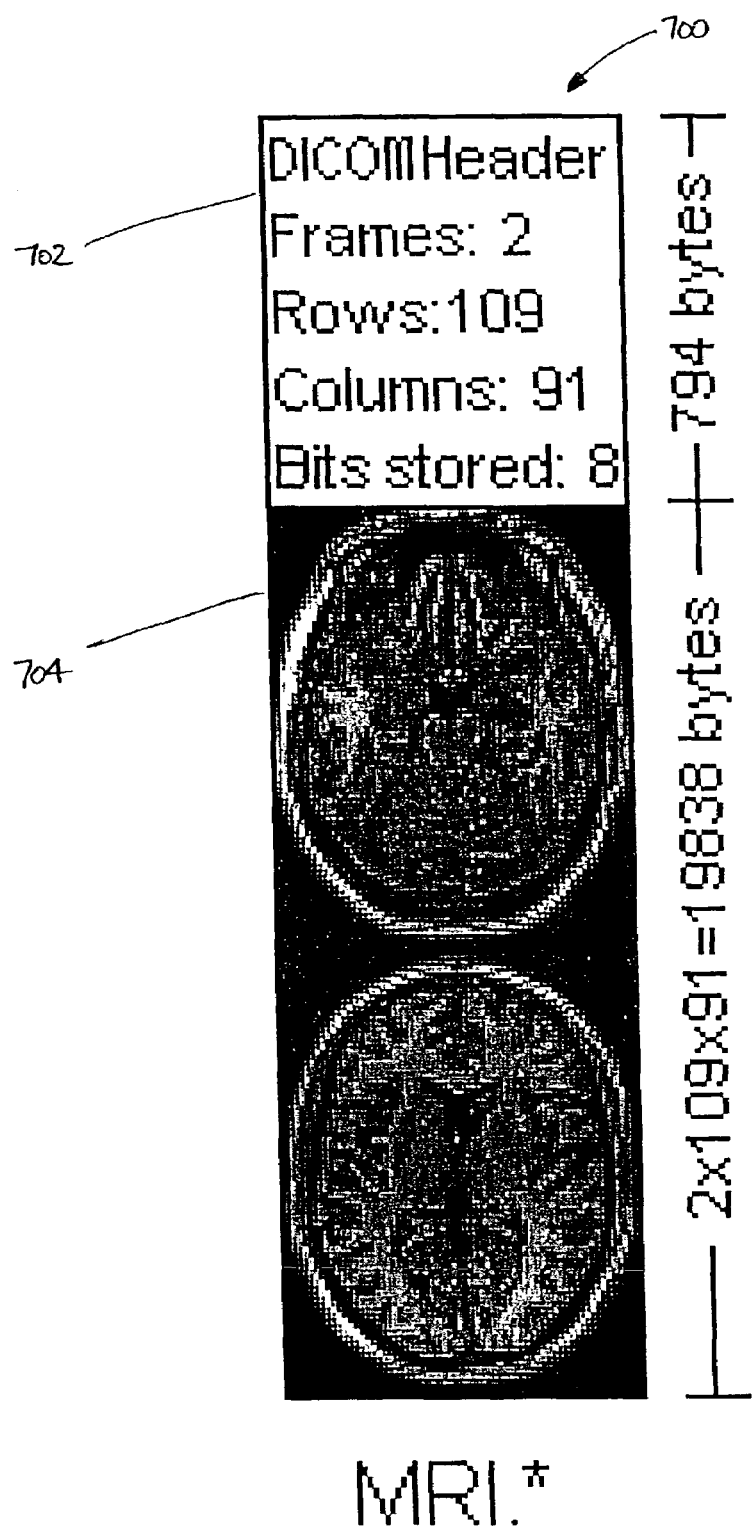
FIG. 7 shows a representative illustration of data contained in a DICOM image file.

An associated application program 101 can be a DICOM application program such as a medical imaging program or an application program capable of communicating with the communications module 100 using a DICOM communications protocol or DICOM standard. The associated application program 101 may execute on one or more clients, medical imaging devices, storage devices, information systems, databases, printers, workstations, acquisition modules, modalities, viewing systems, DICOM media, digital archives, or other types of devices capable of operating using a DICOM communications protocol or DICOM standard. Representative examples of DICOM image files and associated information contained in a DICOM image file are shown in FIGS. 7-8.

The communications module 100 includes a communications engine 104, a data element source 106, a data element sink 108, a state machine 110, a buffer 112, and a multiple-layer protocol such as a DICOM protocol 114. A communications engine 104 is configured for handling data and associated data elements between the associated application program 101 and the communications module 100, as well as between the communications module 100 and the DICOM network 102. The communications engine 104 can also be configured to transmit data and associated data elements between the various components of the communications module 100 as well as between the multiple layers of the DICOM protocol 114. A communications module according to other embodiments may have a fewer or greater number of elements providing similar features.

The data element source 106 is a conceptual source for data elements. A data element source 106 can function as a forward iterator over a conceptual set of data elements. A data element source 106 can provide data elements one at a time, or in a block, to a Service Class User (SCU) or a Service Class Provider (SCP) such as client or server 128*a-n*. For example, a data element source 106 can handle sequence data (SQ) elements.

A data element source 106 can also include a pixel data decoder. A pixel data decoder handles pixel data incrementally, or one at a time. For example, a pixel data decoder handles pixel data (PD) elements. Since a single pixel data element can contain several megabytes of data, a pixel data decoder permits the reading of the pixel data in relatively small, fixed size chunks of data. When a pixel data element is encountered, the pixel data decoder does not read the entire data element at once, but instead the pixel data is read incrementally into a fixed size buffer, such as the buffer shown as 112.

A data element source 106 can include streaming data elements. Similarly, streaming data elements can be handled incrementally.

The data element sink 108 is a conceptual storage for data elements. A data element sink 108 can write data elements one at a time, or in a block, to a Service Class User (SCU) such as client or server 128*a-n*. For example, a data element sink 108 can handle sequence data (SQ) elements.

A data element sink 108 can also include a pixel data encoder. A pixel data encoder handles pixel data incrementally, or one at a time. For example, a pixel data encoder handles pixel data (PD) elements. Since a single pixel data element can contain several megabytes of data, a pixel data encoder permits the writing of the pixel data in relatively small, fixed size chunks of data. When a pixel data element is encountered, the pixel data encoder does not write the entire data element at once, but instead the pixel data is written incrementally into a fixed size buffer, such as the buffer shown as 112.

A data element sink 108 can include streaming data elements. Similarly, streaming data elements can be handled incrementally.

The state machine 110 initiates, monitors, and handles an association or connection between a Service Class Provider (SCP) and a Service Class User (SCU).

The buffer 112 is a memory storage device configured to store data elements, data values, or other types of data. The buffer 112 can also include one or more smaller buffers or similar types of memory storage devices for storing data elements, data values, or other types of data.

The DICOM protocol 114 contains multiple layers including a Transport layer 116, an Upper Level Service layer 118, a Data Service Layer 120, and a Service Class layer 122. The specifications, functionality, and more detailed description of the DICOM protocol and the associated layers 116-122 are set forth in the standards document Digital Imaging and Communications in Medicine (DICOM), PS 3.1-2000, National Electrical Manufacturers Association, 2000, which is incorporated herein by reference.

The communications module 100 communicates with the associated application program 101. The communications module 100 can also communicate with another application program 130 through a communications network such as the DICOM network 102. Typically, another application program 130 will communicate via the DICOM network with the communications module 100 through an interface such as a physical layer 124, i.e. ETHERNET, ATM, FDDI, etc. Furthermore, those skilled in the art will recognize that the DICOM network 102 can utilize Transmission Control Protocol/Internet Protocol (TCP/IP) 126 to further facilitate communication with other networks, computers, platforms, and applications. Thus, the communications module 100 can be positioned with the Transport layer 112 adjacent to the TCP/IP 126, thus creating an interface between the DICOM network 102 and the communications module 100. Those skilled in the art will recognize the methods and systems needed to facilitate this configuration.

A DICOM network 102 can include one or more servers 128*a-n* connected in a network configuration as shown In some instances, a DICOM network 102 will be setup to operate in a local area network or LAN configuration.

A server 128*a-n* can include platforms such as clients, medical imaging devices, storage devices, information systems, databases, printers, workstations, acquisition modules, modalities, viewing systems, DICOM media, digital archives, or other types of devices capable of operating using a DICOM communications protocol or DICOM standard. In a DICOM network 102, a server 128*a-n* can be a Service Class Provider (SCP) or a Service Class User (SCU).

Those skilled in the art will be familiar with other configurations of communication networks that operate similar to the DICOM network 102.

An application program 130 can be configured to execute on a server 128*a-n*. Generally, an application program 130 can be a DICOM application program such as a medical imaging program or an application program capable of communicating with the communications module 100 using a DICOM communications protocol or DICOM standard. An application program 130 may execute on other platforms such as clients, medical imaging devices, storage devices, information systems, databases, printers, workstations, acquisition modules, modalities, viewing systems, each of which may connected to the DICOM network 102.

The communications module 100 can also communicate with a media storage module 132 and a meta database module 134. The media storage module 132 is configured to communicate with the communications module 100, and to store digital image data on a temporary or permanent basis. The media storage module 132 can include a storage medium such as a hard drive, a magneto-optical disk drive, a CD-RW drive, a CD-ROM drive, or other similar type of storage medium. Note that the application program 130 can also be configured to be executed from the media storage module 132.

The meta database module 134 is also configured to communicate with the communications module 100, and to store digital image data on a temporary or permanent basis. The meta database module 134 can include a storage medium such as a conventional database for storing digital data.

Figure 2:
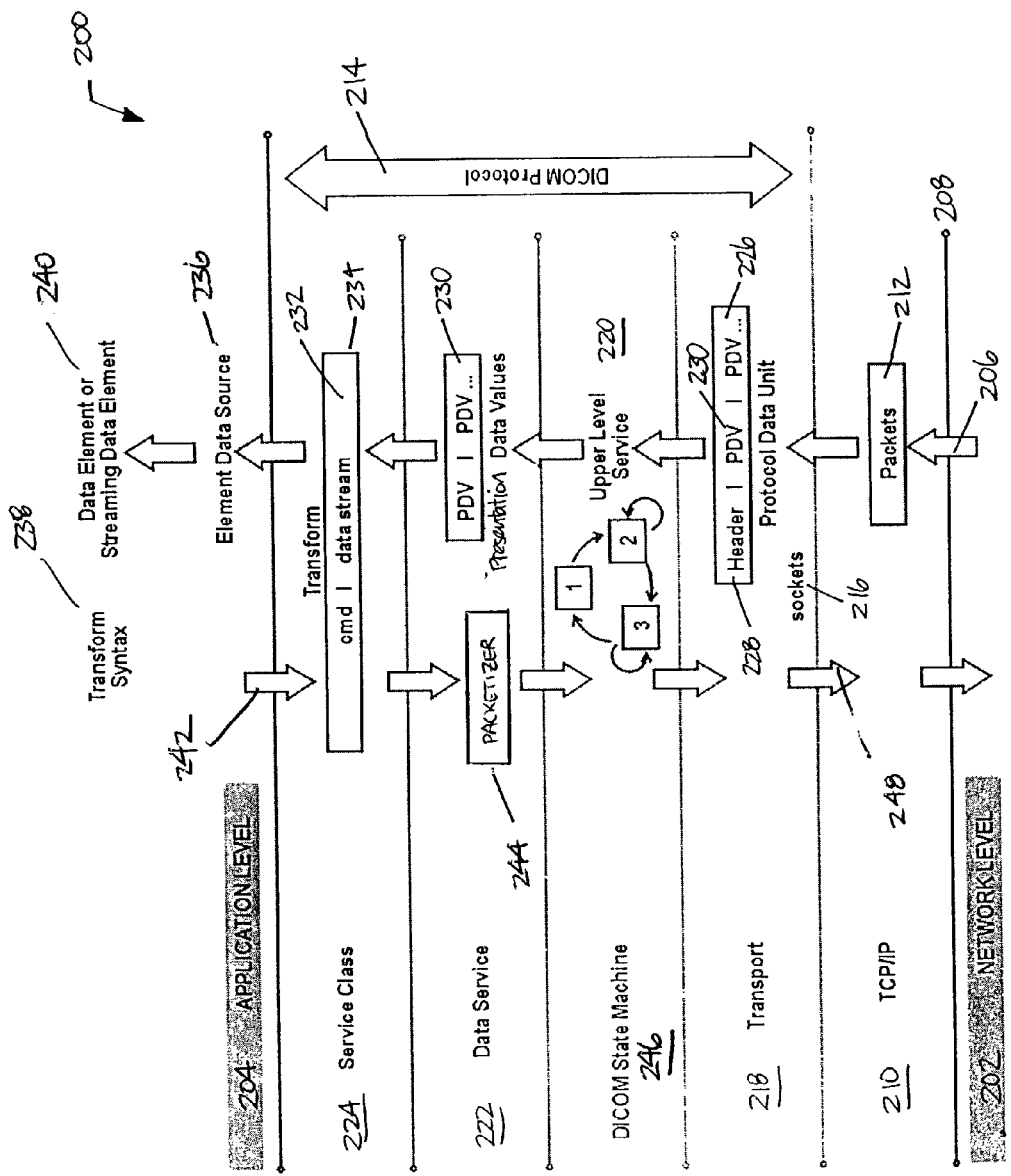
FIG. 2 illustrates a data flow diagram of an exemplary embodiment of the present invention.

FIG. 2 illustrates a generalized data flow diagram of an exemplary embodiment of the present invention. This Figure illustrates an exemplary embodiment of the data flow 200 through multiple layers of the DICOM protocol during transmission of an object or image file between a network and an application. In this example, the network is represented by the network level 202, and the application is represented by the application level 204. With reference to the elements in both FIGS. 1 and 2, the network level 202 can include a DICOM network 102 with a server 128a-n. The application level 204 can include an associated application program 101 such as a medical imaging program associated with the communications module 100. Alternatively, the application level can include an application program 130 executing on another server 128a-n, i.e. a DICOM protocol-capable device such as client computer, in the DICOM network 102. The communications module 100 facilitates data communication between an associated application program 101 and the server 128a-n by creating an association or connection between the associated application program 101 and the server 128a-n. The communications module 100 then handles standard DICOM network protocol details such as determining which Service Object Pair (SOP) classes will be used, defining the roles of the SCP and SCU, negotiating the type of transfer syntax used to communicate between protocol layers, and determining other communication parameters according to a DICOM network protocol or similar type of protocol for handling objects or digital images. Note that in alternative configurations, other devices may be function as a SCP, SCU, or may function as both a SCP and SCU.

Moreover, the communications module 100 can be used to transmit or stream digital data between two devices, such as memory storage devices, hard drives, CD-R, CD-RW, or any other combinations of two different memory storage devices. Those skilled in the art will realize that the communications module 100 can also be used to transmit digital data between other configurations such as between a network-to-device, or device-to-network, wherein the device can include memory storage devices, hard drives, CD-R, CD-RW, or any other similar types of devices.

Furthermore, the communications module 100 negotiates with the associated application program 101 and the server 128a-n to define a maximum size of protocol data unit (PDU) that will be transmitted between the associated application program 101 and server 128a-n. The maximum size of the PDU can depend upon the current size of the memory storage available and the overall performance of the communication network.

Moreover, the communications module 100 can negotiate to define a predefined or limited number of presentation data values (PDVs) that can be read into a presentation data value input stream. The predefined or limited number of presentation data values (PDVs) can depend upon the current size of the memory storage available and/or the overall performance of the communication network. Alternatively, the communications module 100 can negotiate to define a predefined or limited size of data elements that can be read into a data input stream. The predefined or limited size of data elements can depend upon the current size of the memory storage available and/or the overall performance of the communication network. Depending upon the type of data element being handled by the communications module 100, one or more of these techniques may be used to limit the consumption of memory resources to a relatively small, fixed amount of memory during the transmission of the particular data element by the invention. Note that a presentation data value (PDV) includes a header and a payload that can be an array of bytes.

After the association or connection details described above have been completed by the communications module 100, the communications module 100 proceeds to transmit data 206 from the network level 202 to the application level 204. That is, the communications module 100 processes data 206 received from the server 128a-n (acting as a SCP in this example) and sends the processed data to the associated application program 101 (acting as a SCU in this example). Typically, data 206 is a DICOM object or DICOM image file that includes one or more data elements. The data 206 is first handled by at the network level 202 by the server 128a-n. The server 128a-n transmits the data 206 through a standard network physical layer 208 such as ETHERNET, ATM, FDDI, etc.

Next, the data 206 is transmitted from the standard network physical layer through TCP/IP 210 in the form of one or more data packets 212. TCP/IP 210 converts the data 206 including the DICOM object or DICOM image file into one or more data packets 212. Those skilled in the art will recognize the methods and systems needed to perform this conversion.

The TCP/IP 210 transmits the data packets 212 to a DICOM protocol layer 214 using sockets 216. The DICOM protocol layer 214 contains multiple layers including Transport 218, Upper Level Service 220, Data Service 222, and Service Class 224. Sockets 216 is an application program interface (API) that facilitates communication between TCP/IP 210 and other network protocols such as the DICOM network protocol. Those skilled in the art will recognize the methods and systems needed to implement TCP/IP 210, the DICOM protocol layer 214, and sockets 216.

TCP/IP 210 transmits the data packets 212 to the first layer of the DICOM protocol layer 214, known as the Transport layer 216. The communications module 100 receives the data packets 212 in the Transport layer 216, and incrementally reads each of the data packets 212 from TCP/IP 210. That is, a communications engine (shown in FIG. 1 as 104) associated with the communications module 100 reads the data packets 212 one at a time using the Transport layer 216. Once the data packets 212 are processed, the communications engine 104 converts the data packets 208 to protocol data units 226. Protocol data units (PDUs) 226 can include a header 228 and one or more presentation data values (PDVs) 230.

Each PDU 226 is then passed from the Transport layer 218 to the Upper Level Service layer 220 by the communications engine 104. The PDU can then be transmitted to the Data Service layer 222.

The communications engine 104 then extracts the presentation data values (PDVs) 230 from each PDU 226 received by the Data Service layer 222. Generally, the communications engine 104 creates a Presentation Data Value Input Stream (PDVIS) 232 from the PDVs 230. The communications engine 104 forms a message 234 using the PDVIS 232.

The communications engine 104 transmits the message 234 containing the PDVIS 232 to the Service Class layer 224. At the Service Class layer 224, a data element source 236 extracts the data elements from the Presentation Data Value Input Stream (PDVIS) 232 from each message. The data element source 236 becomes the new input transfer syntax (ITS) 238 that can be used to parse the data contained in the PDVIS 232.

At the application level 204, the input transfer syntax 238 extracts data elements 240 from the input stream of bytes and utilizes the data elements 240 as needed by the associated application program 101. The input transfer syntax 238 has an attribute called a streaming threshold. If the extracted data element is longer than the streaming threshold, then the data element 240 will be a streaming data element. The streaming data element is a proxy for the actual data element 240 which is still present in the input transfer syntax 238. The streaming data element allows incremental access to its value using the input transfer syntax 238. The incremental access is provided by a block of data which the streaming data element fills.

For the downward data flow 242 from the application level 204 towards the network level 202, a data element source 236 is first moved through the Service class 224. The data element source 236 then passes to the Data Service 222. At the Data Service 222, a packetizer 244 takes the data element source 236 and creates an output transfer syntax 238. The output transfer syntax 238 processes each of the data elements from the data element source 236, and passes the encoded data elements to the packetizer 244. The packetizer 244 then takes the encoded data elements and creates a presentation data value (PDV).

When PDV is created, the PDV is passed to the DICOM state machine 246 to be processed. The PDV is then handed to the Transport level 218 by the DICOM state machine 246. The Transport level 218 writes out the PDV to the TCP/IP layer 210 via an output stream of bytes 248 which is the network connection.

The exemplary data flow described above with reference to FIG. 2 uses only a limited, fixed amount of memory to process relatively large DICOM objects. The memory used can be described in terms of the memory usage scenario as follows. A DICOM object sent from the network level to the application level can be approximately 600 megabytes (MB) in size of which approximately 599 MB may be pixel data (PD) elements. A maximum protocol data unit (PDU) size is negotiated during the association or connection, for a maximum size of approximately 20 kilobytes (KB). Furthermore, the association or connection can define the maximum number of presentation data values (PDVs) in the presentation data value input stream (PDVIS) as a predefined limit, i.e. a maximum number of five (5). Note that the predefined limit can be selected depending upon the size of a buffer or memory storage device used to store presentation data values (PDVs).

If the PDVIS limits the number of PDVs to five (5), the maximum amount of memory required to read the DICOM object from the network is (5×20 KB)+20 KB, or 120 KB. The "+20 KB" accounts for the PDUs waiting to be placed in the PDVIS.

The application program will then write the incoming DICOM object to a file, passing the input transfer syntax (ITS) as a data element source to the output transfer syntax (OTS) for the file. The OTS will use approximately 10 KB to encode the pixel data elements. All other data elements can be encoded individually as a whole, except for sequence data (SQ) elements. Since all other data elements are normally relatively smaller than 10 KB, the maximum amount of memory used to decode the data elements to file should be 10 KB.

Thus, the total amount of memory used to decode from the network and used to encode the file should be approximately 120 KB to decode and 10 KB to encode, or 130 KB total.

Figure 3A:
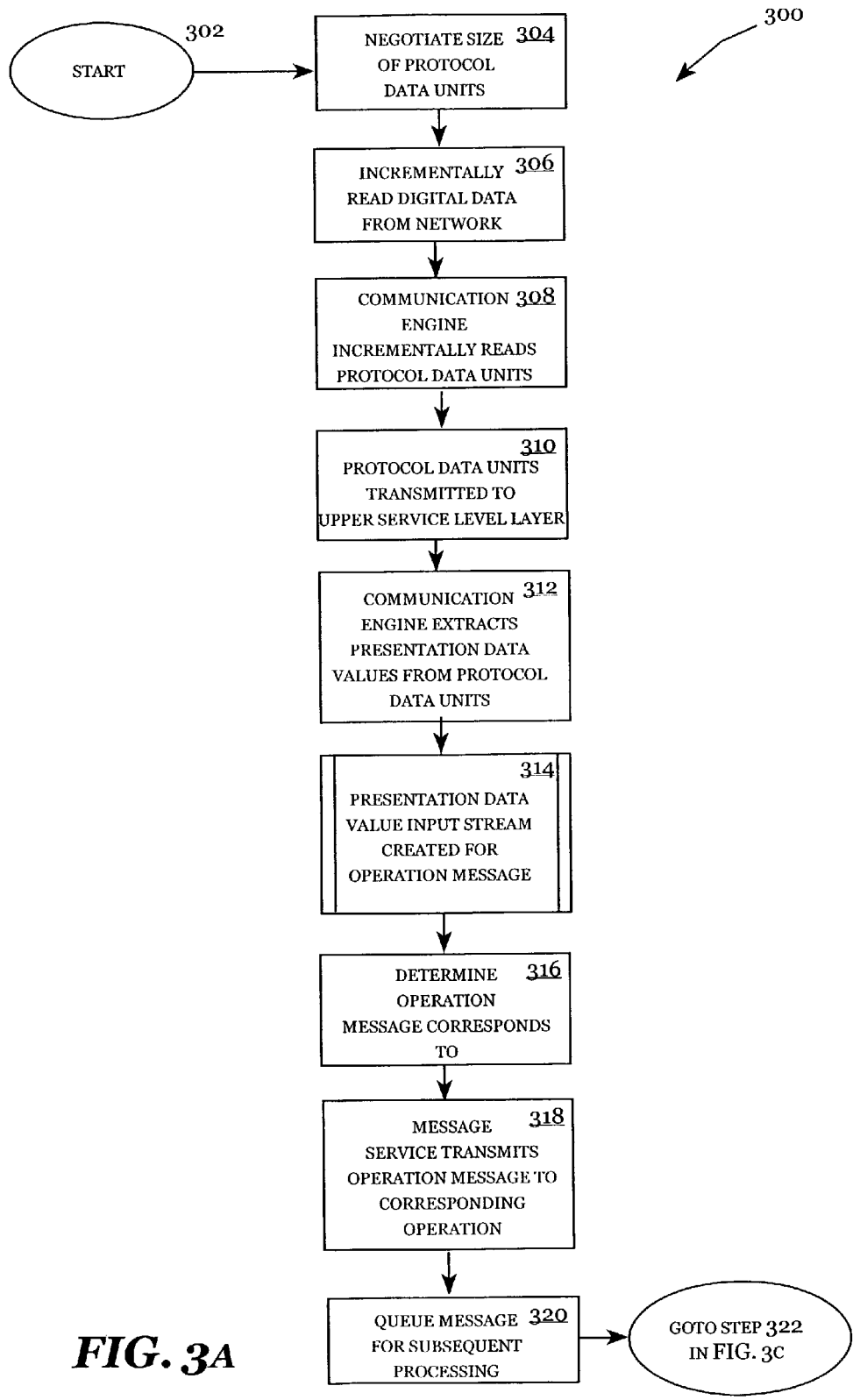
FIGS. 3a-c illustrate an exemplary method of the present invention.
Figure 3B:
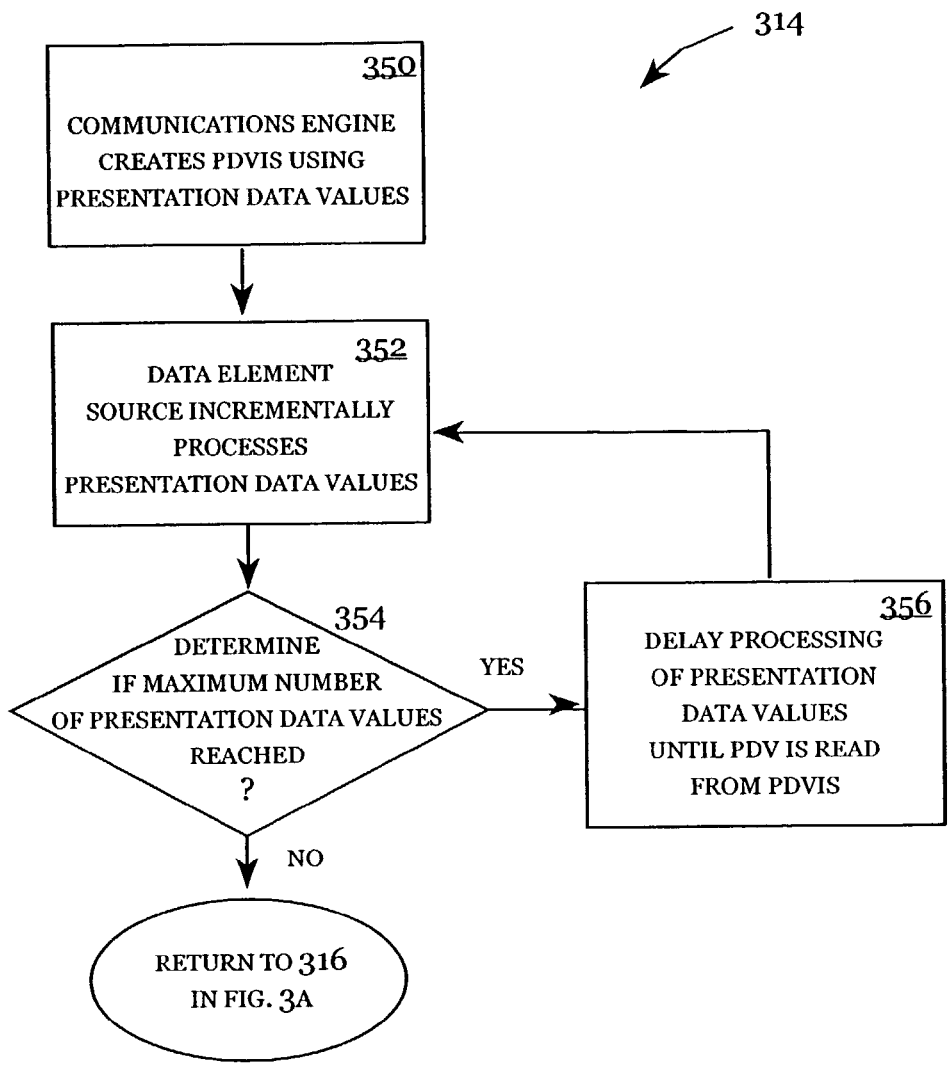
Figure 3C:
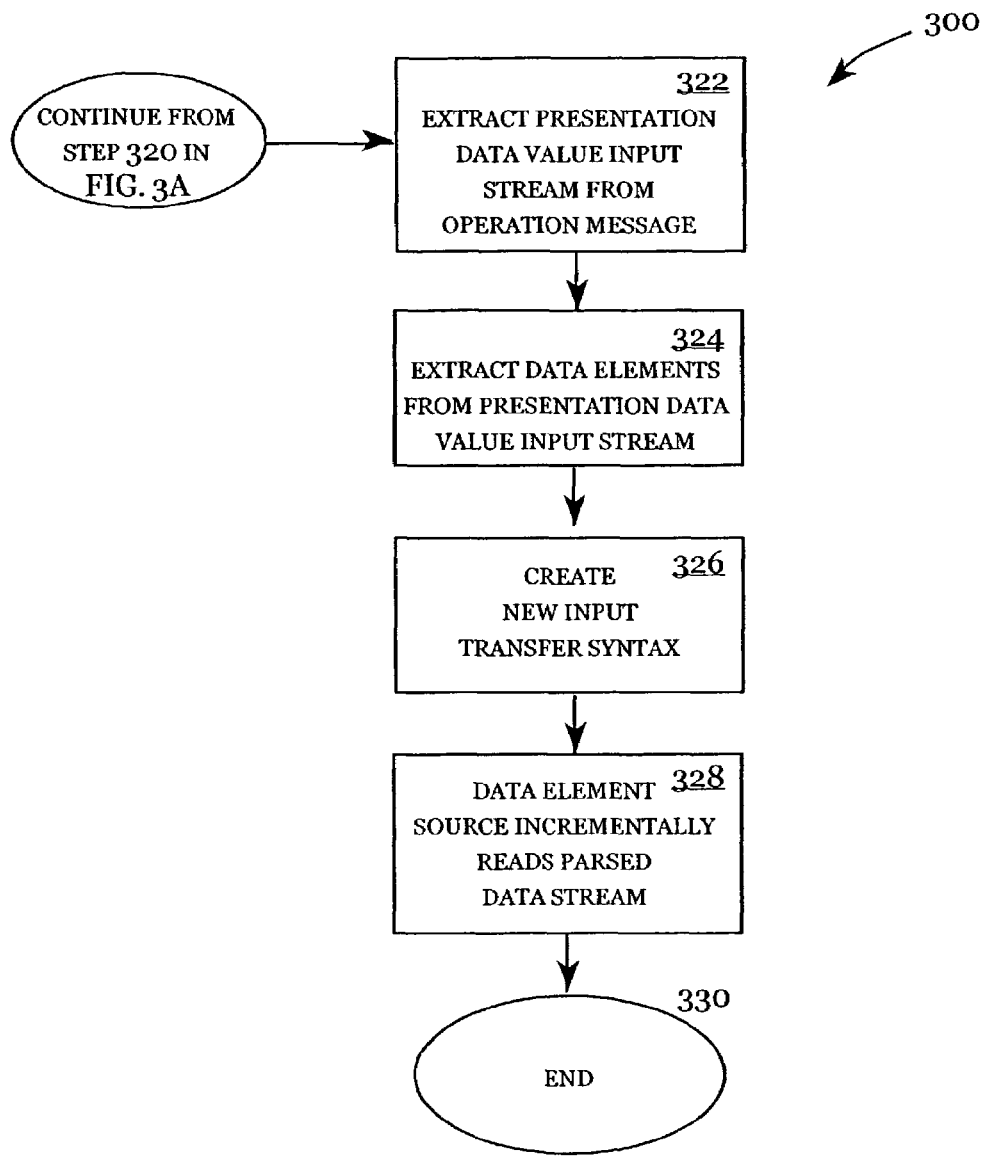
Figure 4A:
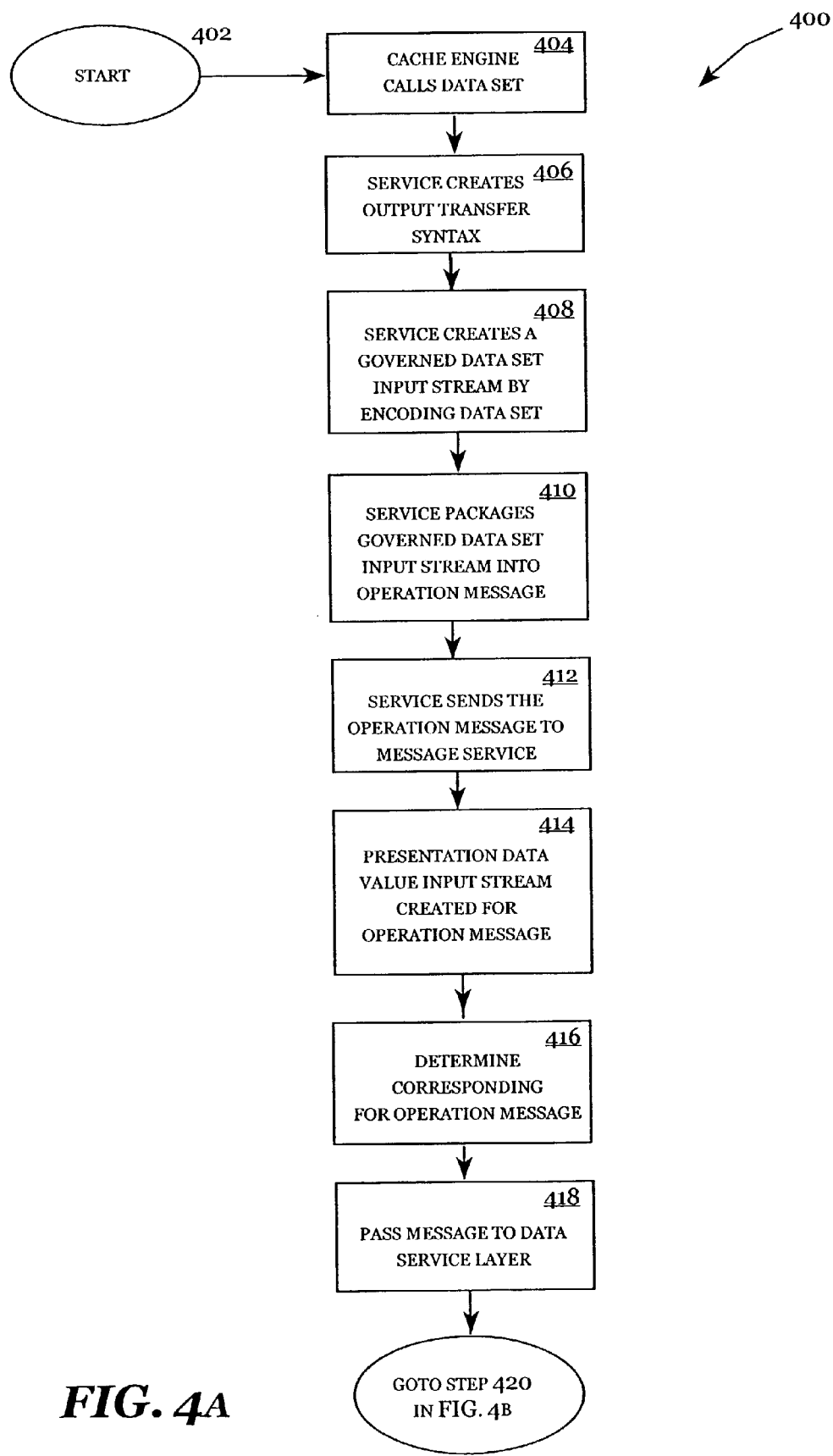
FIGS. 4a-b illustrate a second exemplary method of the present invention.
Figure 4B:
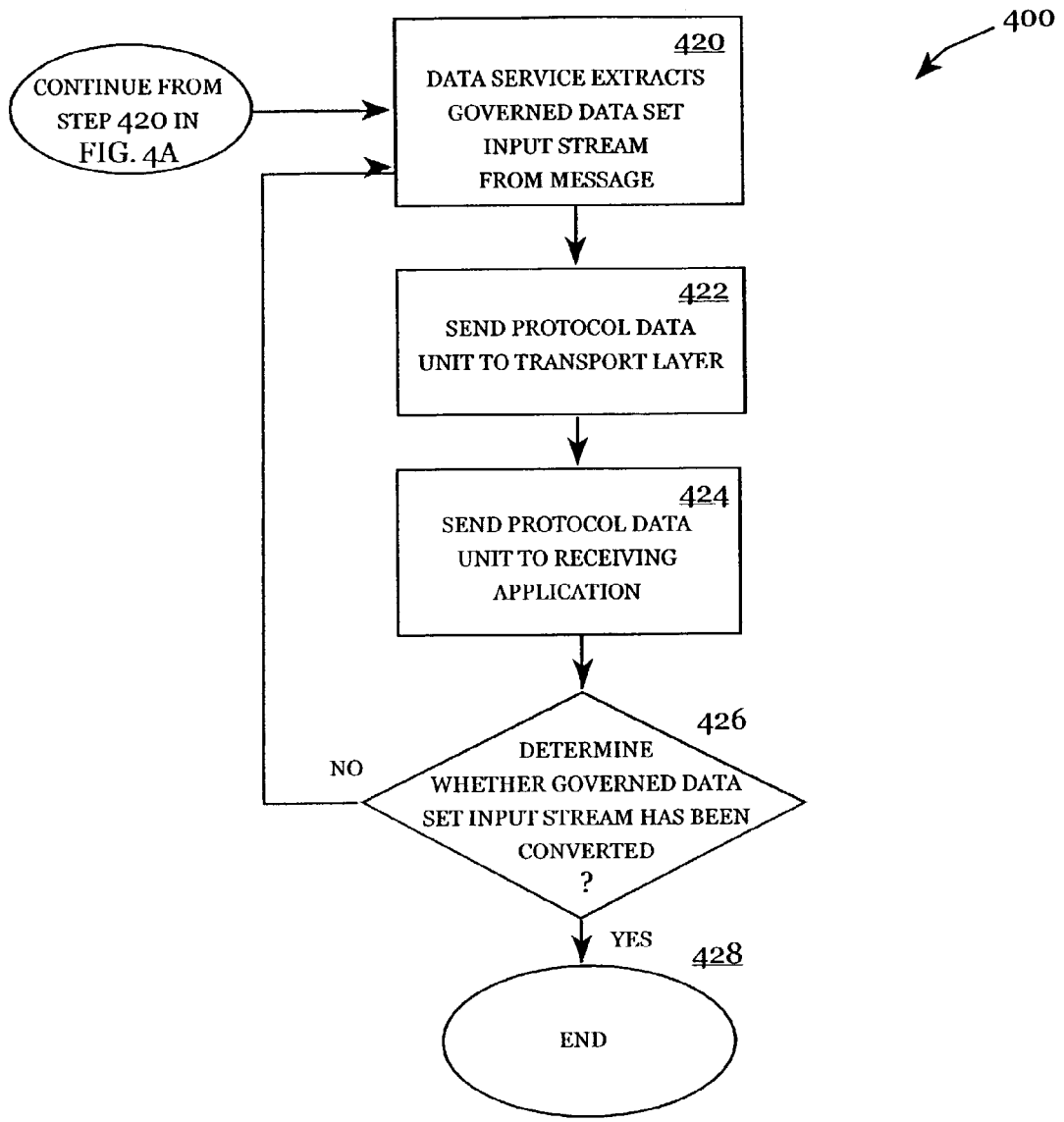
Figure 5:
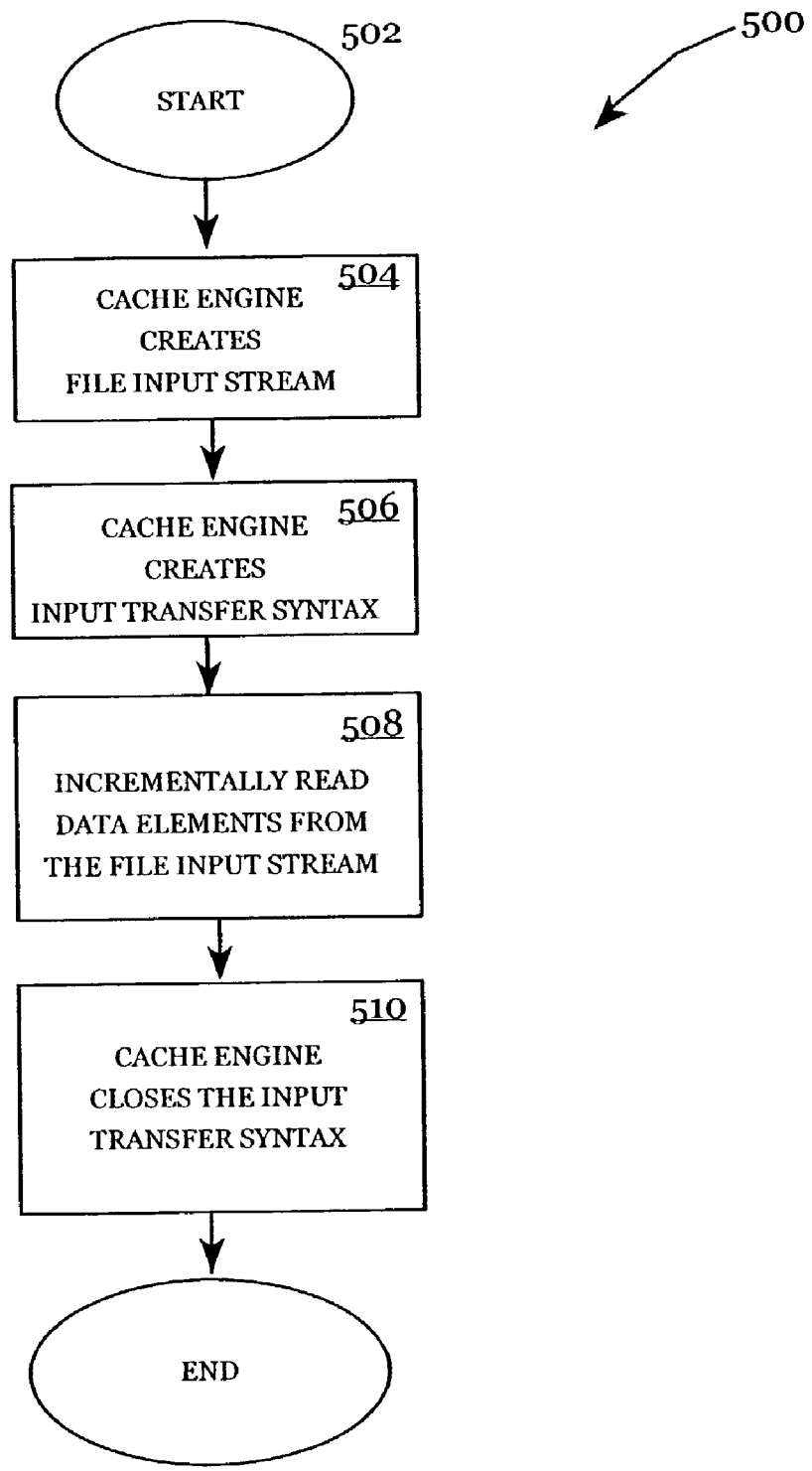
FIG. 5 illustrates a third exemplary method of the present invention.
Figure 6:
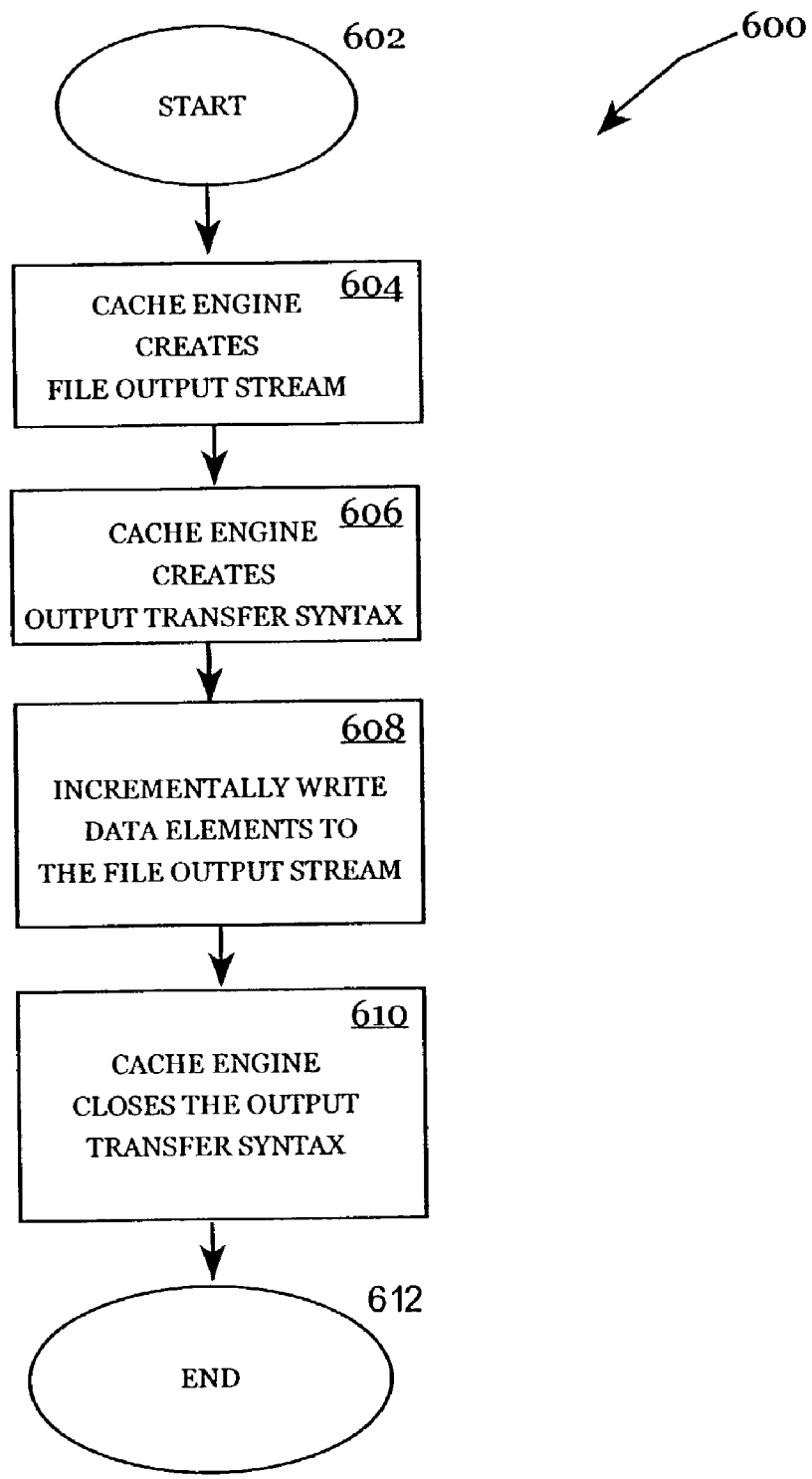
FIG. 6 illustrates a fourth exemplary method of the present invention.

FIGS. 3-6 illustrate flowchart diagrams of exemplary embodiments of methods utilized by the present invention. FIGS. 3a-c and FIGS. 4a-b depict network operations such as reading from and writing to a network. FIGS. 5 and 6 show file operations such as reading from and writing to a file. Utilization of the methods shown in FIGS. 3-6 permit handling of all possible DICOM data interactions using only a relatively small, fixed amount of memory. These DICOM data interactions include DICOM network interactions such as reading and writing data from network to a memory storage device; reading and writing data from a memory storage device to network; and reading and writing from network to network. Note that other types of DICOM data interactions using different configurations of memory storage devices and a network can be performed by the invention.

FIGS. 3a-c depict a method 300 for reading digital data from a network to an application. Generally, the digital data is a DICOM object or image file, the network is a DICOM communications network, and the application is a medical imaging application program capable of communicating using a DICOM network protocol. The method 300 begins at 302.

304 follows 302. In 304, a communications engine 104 negotiates the size of protocol data units (PDUs). Establishing the size of PDUs permits the communications engine 104 to monitor the amount of memory in the buffer 112 needed or desired to process the digital data. Furthermore, a predefined number, limit, or size of presentation data values (PDVs) or another type of data element or quality can also be established by the communications engine 104 depending upon the amount of memory storage in the buffer 112 needed or desired to process the digital data. Typically, these steps are executed in conjunction with the establishment of an association or connection between a Service Control Provider (SCP) and a Service Control Unit (SCU) by the state machine 110. The communications engine 104 through the Upper Level Service layer 118 monitors and controls the state machine 110 throughout the method 300.

304 is followed by 306, in which the communications engine 104 incrementally reads digital data from a network. For example, the communications engine 104 requests digital data such as a DICOM image file from a server 128a-n in a DICOM network 102. The DICOM image file can include one or more sets of digital image data. The server 128a-n transmits the digital image data sets to the communications engine 104 through TCP/IP 126 via sockets, an application program interface. The communications engine 104 receives the digital image data sets in the form of DICOM packets or protocol data units (PDUs) from the server 128a-n.

Note that one skilled in the art will recognize the methods and systems needed to create and transmit digital data through TCP/IP using sockets. Furthermore, protocol data units (PDUs) and DICOM packets are defined under the DICOM network protocol previously described above.

306 is followed by 308, in which the communications engine 104 incrementally reads each PDU or DICOM packet. That is, the communications engine 104 initiates a read thread (not shown) through the Transport layer 116 of the DICOM protocol 114. The read thread incrementally reads and transmits each of the PDUs or DICOM packets, one at a time, across the Transport layer 116 of the DICOM protocol 114. The read thread continues processing the PDUs or DICOM packets until all of the PDUs or DICOM packets of the digital data to be transmitted from the network have been handled.

308 is followed by 310, in which the communications engine 104 transmits the PDUs to the Upper Level Service layer 118. When the PDUs arrive at the appropriate time during the association or connection, the PDUs are then transmitted to the Data Service layer 120 by the communications engine 104.

310 is followed by 312, in which the communications engine 104 extracts presentation data values (PDVs) from each protocol data unit (PDU). That is, when the PDUs are received at the Data Service layer 120, the communications engine 104 extracts the presentation data values (PDVs) from the PDUs. Each protocol data unit includes one or more presentation data values.

312 is followed by subroutine 314, in which a presentation data value input stream is created for an operation message. Subroutine 314 is described in greater detail with reference to FIG. 3c.

In FIG. 3b, subroutine 314 begins at 350. In 350, the communications engine 104 creates a presentation data value input stream using presentation data values. For the initial or first protocol data units (PDUs), extracted presentation data values (PDVs) received by the communications engine 104 are used to create a presentation data value input stream (PDVIS). For subsequent PDUs, the extracted PDVs can be inserted into an existing presentation data value input stream or a new presentation data value input stream is created when needed. A presentation data value input stream is essentially a string of presentation data values (PDVs) from one or more PDUs that can be transmitted using a relatively small, fixed amount of memory. The presentation data value input stream (PDVIS) forms the basis of an operation message.

The communications engine 104 continues to transmit each extracted PDV incrementally or one at a time to the Data Service layer 120. The Data Service Layer 120 inserts each PDV in a presentation data value input stream (PDVIS) as described above. The PDVIS can be limited to storing a predefined or limited number of PDVs at any given instant of time. Typically, the PDVIS is limited to storing five (5) PDVs at a time. Note that the predefined or limited number can be set according to the size of a buffer or other memory storage device to store the PDVs and/or PDVIS.

350 is followed by decision block 352, in which the Data Service layer determines whether the predefined or limited number of PDVs has been reached. In this manner, the transmission of image data can be controlled incrementally to minimize the amount of memory storage space needed to process all of the image data. The data element source 106 processes PDVs incrementally or one at a time, and transmits each PDV to the PDVIS. If a predefined or limited number of PDVs is reached, then the "YES" branch is followed to 354. For example, if the predefined or limited number of PDVs is previously set to five (5), and there is already the predefined or limited number of PDVs in a particular PDVIS, then the limit has been reached. In this manner, the invention can monitor and limit the use of memory to a relatively small, fixed amount of memory that can be used for the transmission of digital data such as DICOM data. Note that in some instances, a predefined or limited size may be set depending upon the size of the buffer 112 or memory storage device. In this manner, pixel data (PD) elements and relatively larger DICOM objects may be handled in relatively small, fixed size portions of data.

In 354, the communications engine 104 delays further processing of presentation data values until a presentation data value can be read from the presentation data value input stream. The communications engine 104 instructs the Data Service layer 120 to wait until a presentation data value (PDV) is read from the presentation data value input stream (PDVIS). That is, the communications engine 104 sends a command to the Data Service layer 120 that temporarily prevents the Transport layer 116 from reading any further PDVs to the PDVIS, until a PDV is read from the PDVIS. When a PDV is read from the PDVIS, the communications engine 104 instructs the Data Service layer 120 to permit the Transport layer 116 to continue to pass PDVs to the PDVIS until the predefined or limited number of PDVs is reached.

Returning to decision block 352, if a predefined or limited number of PDVs is not reached, then the "NO" branch is followed, in which the subroutine 314 ends and the method 300 continues at 316.

In 316, the Message Service determines which operation the operation message corresponds to. Typically, once an operation message is created by the communications engine 104 in subroutine 314, the communications engine 104 sends the operation message including the PDVs and PDVIS to a Message Service (not shown). The Message Service is a component of the Data Service Layer 120 of the DICOM protocol 114.

In the DICOM network protocol, an operation is defined by a Service Object Pair (SOP). During the initial association or connection established by the state machine 110, one or more SOPs can be identified. Utilizing the SOPs, the Message Service determines whether a message has a matching or corresponding operation.

316 is followed by 318, in which the Message Service transmits the operation message to the corresponding operation. When a SOP is identified by the Message Service as a corresponding match for a message, then the operation message is transmitted to the corresponding operation.

318 is followed by 320, in which the operation message is queued by the corresponding operation for subsequent processing. Once the message is queued, the method 300 continues at 320 in FIG. 3c.

320 is followed by 322, in which the queued messages are processed by each respective operation. All of the operations that receive at least one queued operation message will initiate a thread. For each operation, each thread then processes each queued operation message one at a time. Each queued operation message is then passed to the corresponding Service that the operation message was created for. Note that each operation has a corresponding Service or SOP, as defined by the DICOM network protocol. Each thread continues to process each operation message until each queued message for each respective operation has been processed.

322 is followed by 324, in which the Service extracts data elements from the presentation data value input stream (PDVIS).

324 is followed by 326, in which the Service creates a new Input Transfer Syntax (ITS). The Service utilizes the presentation data value input stream (PDVIS) to create a new ITS that can be used to parse the data contained in the PDVIS. The data contained in the PDVIS will be a series of presentation data values (PDVs). Typically, the data values are encoded, and the input transfer syntax can be used to convert the coding to a representation that can be understood as a standard memory representation for the data elements. The parsed data can then be streamed by the communications engine 104 to a data element source 106.

326 is followed by 328, in which the data element source 106 incrementally reads the parsed data stream. Each Service utilizes the data element source 106 to read one block of data elements at a time from the data stream contained in the presentation data value input stream (PDVIS). The input transfer syntax (ITS) can also be utilized to incrementally read the data elements through the data element source 106.

At least two types of data elements can be handled by the Service at the data element source 106: sequence data (SQ) and pixel data (PD). The SQ data element can be a data element that contains one or more sets of data elements. SQ data elements can be processed recursively. That is, a set of data elements can be processed one data element at a time. The PD element is one of the largest data elements in a DICOM object or image file. The PD elements can be composed of a raw data array of bytes (8-bit) or words (16-bit). This type of data element allows additional layers of streaming. The Service can obtain pixel data incrementally, thus minimizing the need to obtain all of the PD values in memory at a single instance of time. Note that pixel data (PD) elements and other DICOM objects can be relatively large. The invention allows pixel data (PD) elements and DICOM objects of all sizes to be handled in relatively small portions over time.

326 is followed by 328, in which the method 300 ends.

FIGS. 4a-b illustrate a second exemplary method of the present invention. As follows, FIGS. 4a-b describe a method 400 for writing data from an application to a network or to another application. Generally, the data is a DICOM object or image file, the network is a DICOM communications network, and the application is a medical imaging application program capable of communicating using a DICOM network protocol.

In 402, the method 400 begins.

402 is followed by 404, in which the communications engine 104 calls upon a data set. Typically, when a user interacts with an associated application program 101, or alternatively, an application program 130 executing on a server 128a-n in a DICOM network 102, the user may desire to perform a particular function on a particular DICOM object or image. The user may select a corresponding command function in the associated application program 101 or application program 130 that corresponds with a particular Service of the application program 101, 130 or network 102. Upon receipt of the command function, the Service locates a corresponding data set for the communications engine 104. Note that a data set can be one or more data sets, each data set comprising one or more data elements. The data set for a DICOM object or image can be stored in an associated memory device such as a media storage module 132 or meta database module 134.

404 is followed by 406, in which the selected Service creates a new output transfer syntax (OTS) for the data set. When a Service receives a command function, the Service creates a new output transfer syntax (OTS) to handle the data set. The OTS can format and convert a data set into a data stream such as a byte stream. The data set may be a data element source. The OTS can also format and convert a data element source into a data stream such as a byte stream. A data element source (DES) is a forward iterator over a conceptual set of data elements. For example, an input transfer syntax (ITS) can produce a data element source (DES) for a particular set of presentation data values (PDVs).

406 is followed by 408, in which the Service creates a governed data set input stream (GDSIS). Using the output transfer syntax, the Service creates a governed data set input stream (GDSIS). Using its own thread, a GDSIS can then convert a data set or data element source to a data stream such as a byte stream using the output transfer syntax. The GDSIS can convert the data set or data element source to a data stream using only a relatively small, fixed amount of memory.

Typically, the output transfer syntax takes each data element one at a time from the data set or data element source and encodes each data element into a series of data elements or a data stream. At least two different types of data elements can be processed by the output transfer syntax: sequence data (SQ) elements and pixel data (PD) elements. In the case of sequence data (SQ) elements, SQ elements contain sets of data elements. When SQ elements are read by the output transfer syntax (OTS), the OTS recursively processes one data element at a time from one particular set of data elements. In the case of PD elements, PD elements contain a large array of bytes or words. When PD elements are read by the output transfer syntax (OTS), the OTS processes these as chunks or small, fixed sizes of data elements. In any case, only a relatively small, fixed size of memory is used by the OTS to process the data elements. The Service can obtain pixel data incrementally, thus minimizing the need to obtain all of the PD values in memory at a single instance of time. Note that pixel data (PD) elements and other DICOM objects can be relatively large. The invention allows pixel data (PD) elements and other DICOM objects of all sizes to be handled in relatively small portions over time.

408 is followed by 410, in which the Service packages the governed data set input stream in an operation message.

410 is followed by 412, in which the Service sends the message to a Message Service.

414 is followed by 416, in which the Message Service determines the corresponding operation for the message.

416 is followed by 418, in which the Message Service passes the message to the Data Service layer 120.

418 is followed by 420, in which the Data Service layer 120 decodes the governed data set input stream from the message. Generally, the Data Service layer 120 receives the message from the Message Service. The Message Service extracts the governed data set input stream (GDSIS) from the message and reads bytes from the GDSIS. The Message Service continues to read bytes from the GDSIS until the Message Service can construct a protocol data unit (PDU). The method 400 then continues at 420 in FIG. 4b.

420 is followed by 422, in which the Message Service sends a protocol data unit (PDU) to the Transport layer 116. Typically, when the association or connection is open, the Message Service can send the PDU through the Upper Service Level layer 118 to the Transport layer 116.

422 is followed by 424, in which the Transport layer 116 transmits the protocol data unit to a receiving application. Generally, the Transport layer 116 transmits the protocol data unit (PDU) through the TCP/IP layer 126, and then through the DICOM network 102 to the application program 130.

424 is followed by decision block 426, in which the Message Service determines whether all of the data elements have been converted to a byte stream by the data element source 106. If all of the data elements have been converted, then the "YES" branch is followed to 428.

In 428, the method 400 ends.

Returning to decision block 426, if not all of the remaining data elements have been converted, then the "NO" branch is followed to 420. The method 400 returns to 420 as necessary to complete processing of the governed data set input stream (GDSIS).

FIG. 5 illustrates a third exemplary method of the present invention. FIG. 5 describes a method 500 for reading data from a file. Generally, the data is a DICOM object or image file, and the file can be associated with an associated application program 101 or application program 130 such as a medical imaging program capable of communicating using a DICOM protocol. The file may be previously stored on a storage device or system such as a server 128a-n operating in conjunction with a communications network such as DICOM network 102, or a media storage module 132, or meta database module 134 as described previously. In FIG. 5, the method 500 begins at 502.

502 is followed by 504, in which the communications engine 104 creates a file input stream for an image file. A file input stream can be an input stream of bytes. Typically, when a user decides to read image data or objects from a file, the user selects an application command to read an object or image file. For example, an associated application program 101 can permit a user to select a command to read a file containing a DICOM object or image file. When the particular command is selected, the associated application program 101 then creates a file input stream for the DICOM object or image file to be read in a system containing the DICOM object or image file. The file input stream is a forward iterator over a portion of bytes or data elements in a file. The file input stream can be read from the beginning to the end in a single direction. The system can be a server 128*a-n*, media storage module 132, or meta database module 134 as defined previously.

504 is followed by 506, in which the communications engine 104 creates an input transfer syntax (ITS) to read the image file. Generally, the communications engine 104 creates an input transfer syntax (ITS) using the previously created file input stream. The input transfer syntax can then be used to read data elements from the corresponding object or image file.

506 is followed by 508, in which the data element source 106 incrementally reads each data element from the file input stream. The data element source 106 utilizes the input transfer syntax (ITS) to incrementally read one data element or one block of data elements at a time from the file input stream. At least two different types of data elements can be processed: sequence data (SQ) elements and pixel data (PD) elements. In the case of sequence data (SQ) elements, SQ elements contain sets of data elements. When SQ elements are read by the input transfer syntax (ITS), the ITS recursively processes one data element at a time from one particular set of data elements. In the case of PD elements, PD elements contain a large array of bytes or words. When PD elements are read by the input transfer syntax (ITS), the ITS processes these as chunks or small, fixed sizes of data elements. In any case, only a relatively small, fixed size of memory is used by the ITS to process the data elements.

508 is followed by 510, in which the communications engine 104 closes the input transfer syntax (ITS). That is, after all of the data elements have been read by the data element source, the communications engine closes the input transfer syntax is closed and no further processing of the data elements is performed by the data element source 106.

510 is followed by 512, in which the method 500 ends.

FIG. 6 illustrates a fourth exemplary method of the present invention. FIG. 6 describes a method 600 for writing data to a file. Generally, the data is a DICOM object or image file, and the file can be associated with an application such as a medical imaging program capable of communicating using a DICOM protocol. The file may be previously stored on a storage device or system such as a server operating in conjunction with a network such as DICOM communications network. In FIG. 6, the method 600 begins at 602.

602 is followed by 604, in which the communications engine 104 creates a file output stream. A file output stream can be a output stream of bytes. Typically, when a user decides to write image data to a file, the user selects a command from an associated application program 101 or application program 130 to write data to an object or image file. For example, an associated application program 101 can permit a user to select a command to write image data to a file configured for storing a DICOM object or image. When a particular command is selected, the application program 130 then creates a file output stream for the image data to be written to a system containing the DICOM object or image file. The system can be a server 128*a-n*, media storage module 132, or meta database module 134 as defined previously.

604 is followed by 606, in which the application program 130 creates an output transfer syntax (OTS) to write the image data to the object or image file. Generally, the associated application program 101 or application program 130 creates an output transfer syntax (OTS) using the previously created file output stream. When an output transfer syntax (OTS) is created, the file output stream is one argument used to create the output transfer syntax. The OTS can then be used to write the image data to the corresponding object or image file.

606 is followed by 608, in which a data element sink 108 incrementally writes each data element to the file output stream. That is, the data element sink 108 utilizes the output transfer syntax (OTS) to incrementally write one data element or one block of data elements at a time to the file output stream. As described in FIG. 5 above, at least two different types of data elements can be processed: sequence data (SQ) elements and pixel data (PD) elements. In the case of sequence data (SQ) elements, SQ elements contain sets of data elements. When SQ elements are written by the output transfer syntax (OTS), the OTS recursively processes one data element at a time from one particular set of data elements. In the case of PD elements, PD elements contain a large array of bytes or words. When PD elements are written by the output transfer syntax (OTS), the OTS processes these as chunks or small, fixed sizes of data elements. In any case, only a relatively small, fixed size of memory is used by the output transfer syntax (OTS) to process the data elements.

608 is followed by 610, in which the communications engine 104 closes the output transfer syntax (OTS). That is, after all of the data elements have been written by the data element sink 108 to the file output stream, the output transfer syntax is closed by the communications engine 104, thus effectively closing the file now containing the object or image file.

610 is followed by 612, in which the method 600 ends.

FIG. 7 shows a representative illustration of data contained in a DICOM image file. This particular example is a magnetic resonance image (MRI) DICOM image file 700. In this example, the first 794 bytes are used for a DICOM format header 702. The format header 702 describes the image dimensions and retains other text information about the scan. The size of this header 702 varies depending upon how much header information is stored. The example shows the dimensions of the image as 109×91×2 pixels, with a resolution of 1 byte per pixel, thus the total image size will be approximately 19,838 bytes.

Image data 704 is stored in the file portion following the header 702. The image data is also stored in the same file as the header 702 and associated information.

FIG. 8 illustrates data contained in a DICOM image file. In this example, the DICOM header format requires a 128-byte preamble. Typically, in a DICOM header format, the 128 byte preamble is usually set to zero. The 128-byte preamble is then followed by the letters "D", "I", "C", and "M". Header information then follows the last letter "M". The header information can be organized into one or more portions called "groups". For example, a group "0002hex" can designate the file meta information group. This group can define three elements such as group length, file version, and transfer syntax. The DICOM data elements defined in each group depends upon the image type. A representative sample of data elements that can be defined is listed in Part 3 of the 2000 DICOM standard. For example, a magnetic resonance (MR) image file can be designated by element 0008,0060. This type of image file can include one or more elements to describe MRI echo time.

Alternative embodiments will become apparent to those skilled in the art to which the present invention pertains without departing from its spirit and scope. Accordingly, the scope of the present invention is defined by the appended claims rather than the foregoing description.

We claim:

1. A method for communicating Digital Imaging and Communications in Medicine (DICOM) data between two devices in a network, wherein the data comprises data elements, the method comprising:
providing a plurality of data elements from a first device;
providing a streaming threshold, wherein the streaming threshold comprises:
a maximum size of data elements to be transmitted between the first device and a second device, wherein the first device is a Service Class Provider capable of providing data packets and the second device is a Service Class User capable of receiving an output stream of bytes; and
a maximum number of data elements to be encoded in a data stream to be transmitted between the first device and the second device;
based at least in part on the streaming threshold, encoding at least some of the plurality of data elements into the data stream to be transmitted between the first device and the second device;
defining a limited number of presentation data values to be stored in the data stream, wherein the limited number is based at least in part on either a size of a storage device or performance of the network;
incrementally reading a set of data packets from the Service Class Provider so that each data packet is read one at a time;
creating the presentation data value stream with only a limited number of presentation data values;
incrementally reading pixel data elements one at a time from the data stream into the storage device, wherein an entire data element is incrementally read in small, fixed size portions into the storage device;
transmitting at least a portion of the stored data elements to the second device;
transmitting a presentation data value stream containing the limited number of presentation data values to a second Service Class Provider if the predefined limit of presentation data values is reached; and
extracting the presentation data values from the presentation data value stream.

2. The method of claim 1, wherein at least one of the devices is a file system comprising at least one selectable file configured for conversion to a stream of bytes, and wherein a data element source can be created.

3. The method of claim 2, wherein the data element source comprises an input transfer syntax.

4. The method of claim 1, wherein the network comprises a network connection configured for providing a data stream.

5. The method of claim 4, wherein the data stream comprises protocol data units containing presentation data values, the presentation data values comprising byte arrays.

6. The method of claim 4, wherein at least one byte arrays can be placed in a presentation data value input stream.

7. The method of claim 6, wherein the data element source comprises an input transfer syntax created from the presentation data value input stream.

8. The method of claim 6, wherein the presentation data value input stream is limited to buffering a predefined or limited number of presentation data values.

9. The method of claim 1, wherein at least one of the devices comprises a file system comprising a file with an output stream of bytes.

10. The method of claim 9, wherein a data element sink can be created from the output stream of bytes.

11. The method of claim 10, wherein the data element sink comprises an output transfer syntax created from the output stream of bytes.

12. The method of claim 1, wherein the network comprises a network connection configured for receiving an output stream of bytes.

13. The method of claim 12, wherein the output stream of bytes comprises a packetizer configured to create protocol data units containing presentation data values.

14. The method of claim 13, wherein the data element sink provides bytes to the packetizer.

15. The method of claim 14, wherein the data element sink comprises an output transfer syntax created with the packetizer.

16. The method of claim 1, further comprising a data element source having an input transfer syntax further comprising a streaming threshold configured to provide a byte limit.

17. The method of claim 16, wherein if the byte limit is exceeded by a stream of bytes comprising a data element, then the data element comprises a streaming data element.

18. The method of claim 17, wherein the streaming data element comprises incremental values obtained from the input transfer syntax.

19. The method of claim 1, wherein the data element sink comprises a streaming data element, and the data element sink comprises an output transfer syntax.

20. The method of claim 19, wherein the data element sink requests from the streaming data element values in fixed block size.

21. The method of claim 20, wherein the output transfer syntax encodes the streaming data element values as each block is received.

22. The method of claim 1, wherein at least one of the devices is capable of providing an input stream of bytes.

23. The method of claim 22, wherein at least one of the devices comprises at least one of the following: a database, a tape, a CD, or a storage medium.

24. The method of claim 1, wherein at least one of the devices is capable of receiving an output stream of bytes.

25. The method of claim 1 further comprising:
utilizing input transfer syntax to extract the data elements from the data stream for use by an application program, the input transfer syntax comprising a streaming threshold whereby if the extracted data element is longer than the streaming threshold the extracted data element will be a streaming data element.

26. The method of claim 25, wherein the data elements comprise presentation data values obtained from the input transfer syntax.

27. The method of claim 25 further comprising:
creating an output transfer syntax from said output stream of bytes; and
requesting the presentation data values in fixed block size.

28. The method of claim 27, wherein the output transfer syntax encodes the presentation data values as each block is received.

29. The method of claim 25, wherein employing transfer syntax to extract the data elements from the protocol data units is used to parse the presentation data values contained in the presentation data stream.

30. The method of claim 1, wherein defining a limited number of presentation data values comprises negotiating an association between the Service Class Provider and/or the Service Class User.

31. The method of claim 1, wherein defining a limited number of presentation data values to be stored in the presentation data value stream sets the number of data values at five or less.

32. The method of claim 1, further comprising:
incrementally processing the protocol data units one at a time until all of the protocol data units from all of the presentation data stream have been processed.

33. The method of claim 1, further comprising:
incrementally writing data one at a time into the fixed size buffer.

34. A method for transmitting a Digital Imaging and Communications in Medicine (DICOM) image between two devices in a network, wherein the image comprises a plurality of protocol data units, the method comprising:
providing a plurality of protocol data units from a first device;
providing a streaming threshold, wherein the streaming threshold comprises:
a maximum size of data elements to be transmitted between the first device and a second device, wherein the first device is a Service Class Provider capable of providing data packets and the second device is a Service Class User capable of receiving said output stream of bytes; and
a maximum number of data elements to be encoded in a data stream to be transmitted between the first device and the second device;
based at least in part on the streaming threshold, encoding at least some of the plurality of protocol data units in the data stream, wherein the data stream is based at least in part on a capacity of a storage device;
defining a limited number of presentation data values to be stored in the data stream, wherein the limited number is based at least in part on either a size of a storage device or performance of the network;
incrementally reading a set of data packets from the Service Class Provider so that each data packet is read one at a time;
creating a presentation data value stream with only a limited number of presentation data values;
incrementally storing presentation data values from the data stream in the storage device;
transmitting at least a portion of the stored data stream to a second device using the presentation data values;
transmitting the presentation data value stream containing the limited number of presentation data values to a second Service Class Provider if the predefined limit of presentation data values is reached; and
extracting the presentation data values from the presentation data value stream.

35. The method of claim 34, wherein the data stream comprises at least five presentation data values.

36. The method of claim 34, wherein the storage device comprises at least one of the following: a memory, or a buffer.

37. The method of claim 34, wherein the data stream comprises a the presentation data value input stream.

38. The method of claim 34, further comprising:
encoding the plurality of protocol data units in additional data streams, wherein the additional data streams are each based at least in part on a capacity of an additional storage device;
incrementally storing presentation data values from the plurality of protocol data units in an additional storage device; and
transmitting the additional encoded data streams to the second device using the presentation data values, wherein the image is transferred from the first device to the second device.

39. The method of claim 34, wherein the data stream is further based at least in part on performance of the network.

* * * * *